US011534483B2

(12) United States Patent
Polyakov et al.

(10) Patent No.: US 11,534,483 B2
(45) Date of Patent: *Dec. 27, 2022

(54) COMPOSITIONS FOR THE TREATMENT AND PREVENTION OF HOOF AND CLAW DISEASES

(71) Applicants: Igor Polyakov, Ulm (DE); Liudmila Ivanova, Ulm (DE)

(72) Inventors: Igor Polyakov, Ulm (DE); Liudmila Ivanova, Ulm (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/085,025

(22) PCT Filed: Mar. 15, 2017

(86) PCT No.: PCT/EP2017/056145
§ 371 (c)(1),
(2) Date: Sep. 14, 2018

(87) PCT Pub. No.: WO2017/158039
PCT Pub. Date: Sep. 21, 2017

(65) Prior Publication Data
US 2019/0328853 A1 Oct. 31, 2019

(30) Foreign Application Priority Data
Mar. 15, 2016 (EP) .................................... 16160532

(51) Int. Cl.
| A61K 39/00 | (2006.01) |
| A61P 31/10 | (2006.01) |
| A61K 36/06 | (2006.01) |
| A61K 47/12 | (2006.01) |
| A61K 47/26 | (2006.01) |
| A61K 47/36 | (2006.01) |
| A61K 45/06 | (2006.01) |

(52) U.S. Cl.
CPC .......... *A61K 39/0002* (2013.01); *A61K 36/06* (2013.01); *A61K 47/12* (2013.01); *A61K 47/26* (2013.01); *A61K 47/36* (2013.01); *A61P 31/10* (2018.01); *A61K 45/06* (2013.01)

(58) Field of Classification Search
CPC .............. A61K 39/0002; A61K 31/722; A61K 2039/552; A61K 2039/545; C08B 37/003; C12R 1/645
USPC ...................................................... 424/274.1
See application file for complete search history.

(56) References Cited

U.S. PATENT DOCUMENTS

| 6,290,950 B1 | 9/2001 | Poliakov et al. |
| 2004/0071737 A1* | 4/2004 | Farnow .............. A61K 39/0002 424/274.1 |
| 2014/0256826 A1 | 9/2014 | Lemire et al. |
| 2019/0328853 A1 | 10/2019 | Polyakov et al. |

FOREIGN PATENT DOCUMENTS

| CN | 1199426 A | 11/1998 | |
| CN | 102 727 887 | 7/2012 | |
| EP | 393371 | 10/1990 | |
| EP | 0956042 A2 * | 11/1999 | ......... A61K 39/0002 |
| EP | 3429616 | 9/2017 | |
| RU | 2020959 | 10/1994 | |
| RU | 2074251 C1 | 2/1997 | |
| RU | 2093178 C1 | 10/1997 | |
| UA | 42681 | 11/2001 | |
| UA | 18803 | 11/2006 | |
| UA | 21449 | 3/2007 | |
| UA | 25296 | 8/2007 | |
| UA | 97633 | 3/2012 | |
| UA | 110816 | 2/2016 | |
| WO | WO 93/07894 | 4/1993 | |
| WO | WO 1997/007232 | 2/1997 | |
| WO | WO 98/15284 | 4/1998 | |
| WO | WO 2013/033400 | 3/2013 | |
| WO | WO 2017/001580 | 1/2017 | |
| WO | WO 2017/158039 A1 | 9/2017 | |
| WO | WO 2017/158040 | 9/2017 | |

OTHER PUBLICATIONS

Kuwano et al., (Equine Vet J Suppl. Sep. 1998;(26):27-35) (Year: 1998).*
Database WPI, Week 199741, Thomson Scientific, London, GB; AN1997-446777 & RU2074251C1 (Veterinary Preparations Constol. Res. Inst.) Feb. 27, 1997 (Feb. 27, 1997); Accessed in 2017.
Database WPI, Week 199824, Thomson Scientific, London, GB; AN1998-29979 & RU2093178C1 (Exper Veterinary Res. Inst.) Oct. 29, 1997 (Oct. 29, 1997); Accessed in 2017.
International Search Report and Written Opinion of International Application No. PCT/EP2017/056145, dated Jun. 28, 2017.
Office Communication issued in correspondence Ukrainian Application No. 2018/09800 dated Jun. 4, 2022 {English translation}.
Osová et al., "Interdigital phlegmon (foot rot) in dairy cattle—an update", WTM, 104: 209-220, 2017.
Seferian et al., "Immune stimulating activity of two new chitosan containing adjuvant formulations", Vaccine, 19:661-668, 2001.
Shamov et al., "Interaction of Carboxylic Acids with Chitosan: Effect of pK and Hydrocarbon Chain Length", Journal of Colloid and Interface Science, 249:316-321, 2002.
"ICAR Claw Health Atlas", Ed. Egger-Danner, C., et al. *ICAR Technical Series*, First Edition, Jun. 2015.
Lee, Kuen Yong, Wan Shik Ha, and Won Ho Park. "Blood compatibility and biodegradability of partially N-acylated chitosan derivatives." *Biomaterials* 16.16 (1995): 1211-1216.

(Continued)

*Primary Examiner* — Jana A Hines
(74) *Attorney, Agent, or Firm* — Parker Highlander PLLC

(57) ABSTRACT

The present invention relates to a composition comprising antigenic material of keratinophilic fungi and/or keratinophilic yeasts for use in a method of treating and/or preventing hoof- and claw diseases in animals and a new *Trichophyton verrucosum* strain which can e.g. be used in such a method of treatment and/or prevention.

16 Claims, No Drawings

(56) References Cited

OTHER PUBLICATIONS

Palmer, Maeve A., and Niamh E. O'Connell. "Digital dermatitis in dairy cows: A review of risk factors and potential sources of between-animal variation in susceptibility." *Animals* 5.3 (2015): 512-535.

Wang, Huadong, et al. "An adjuvanted inactivated murine cytomegalovirus (MCMV) vaccine induces potent and long-term protective immunity against a lethal challenge with virulent MCMV." *BMC Infectious Diseases* 14.1 (2014): 1-11.

Wilson-Welder, Jennifer H., David P. Alt, and Jarlath E. Nally. "Digital dermatitis in cattle: current bacterial and immunological findings." *Animals* 5.4 (2015): 1114-1135.

* cited by examiner

COMPOSITIONS FOR THE TREATMENT AND PREVENTION OF HOOF AND CLAW DISEASES

This application is a national phase application under 35 U.S.C. § 371 of International Application No. PCT/EP2017/056145, filed Mar. 15, 2017, which claims priority to European Patent Application No. 16160532.4, filed Mar. 15, 2016. The entire text of each of the above referenced disclosures is specifically incorporated herein by reference.

The present invention relates to a composition comprising antigenic material of keratinophilic fungi and/or keratinophilic yeasts for use in a method of treating and/or preventing hoof- and claw diseases in animals and a new *Trichophyton verrucosum* strain which can e.g. be used in such a method of treatment and/or prevention.

Digital dermatitis (shortly DD, also called Mortellaro's disease or Italian foot rot), which was first described in 1974 by Cheli and Mortellaro, is a big problem in dairy cows and beef cattle and is present on many dairy farms. DD is very infectious and difficult to treat and to prevent. Also, it is difficult to control the elimination from the herd. This disease is causing significant economic losses worldwide. Different kinds of bacteria are responsible for the skin lesions in the interdigital place, which are characterized by red or "strawberry like", hairless and painful ulcer with epithelial hyperplasia and swelling at the affected sites. They are typically located at the back of the foot, in the interdigital space. Inactive or treated lesions may be very difficult to differentiate from other warty digital lesions. DD should be differentiated from interdigital dermatitis (ID), which results in necrosis or necrobacillosis of the distal interdigital skin. Investigations identified bacterial spirochetes in sections of DD tissue. In further analysis many types of bacteria were identified in DD lesions. In particular, *Treponema* spp such as *T. phagedenis, T. vincentii*, and *T. denticola* can develop the clinical sings of DD. A very strong complex of different etiological factors was found.

Interdigital dermatitis (ID) usually occurs in dairy cattle and is one of the main infectious causes of lameness. Exudative dermatitis, wet, and smelly erosions with crust or scab and sole ulcers characterize the clinical manifestation of skin lesions in the heel area and the interdigital space. Also clinical symptoms on the dorsal surface of the digits can be observed. The heels are painful.

Afterwards, hyperplasia (corns, fibroma) with chronic irritation of the interdigital space is often observed resulting in the lameness. A mixture of different bacteria causes ID. *Dichelobacter nodosus* plays an important role in the manifestation of clinical symptoms. This microorganism is an anaerobe with strong photolytic properties. Mostly, the infection is caused by bacteria from infected cows wherein *D. nodosus* spreads from infected to non-infected animals. Although the bacteria cannot survive for long times in the ground they can persist in the claws. The bacteria destroy the epidermis, but do not penetrate the dermal layers. The disintegration of the border between the skin and the soft heel horn produces erosions and ulcers. The lesions cause discomfort.

Interdigital phlegmone (shortly IP, also called panaritium or foot rot) is a necrotic inflammation of the skin in the interdigital space. Manifestation of the disease is usually in an acute or subacute form. The lesions, erosion and injury in the interdigital skin serve as infection atriums. Moreover, bacterial microflora may enter and infect the subcutaneous tissue. Infected animals became lame, cellulitis and swelling. The clinical symptoms of IP are accompanied by a decrease in milk production, decreased appetite and a fever. Mainly, the microorganisms *Dichelobacter nodosus, Staphylococcus aureus, Escherichia coli, Arcanobacterium pyogenes*, and other are involved in IP. The main bacteria involved in IP is *Fusobacterium necrophorum* that is a gram-negative, no spore forming, no flagellated, no motile, pleomorphic anaerobic bacteria. This bacterium produces a lipopolysaccharide endotoxin that has a necrotizing activity and causes necrosis of the skin and subcutaneous tissue.

DD, ID and IP, which are the most common infectious hoof and claw diseases, are sporadically distributed worldwide but may be endemic in particular in intensive beef or dairy cattle production units. The incidence depends amongst other on weather, season of year, grazing periods, and housing system. IP usually leads to lameness and to a significant decrease in body weight, loss of fertility and decrease of milk production. The incidence can be between 5% and 30%. In the first epidemic cases about 30% to 80% animals can show clinical sings of the disease. However, on an average IP accounts only for up to 15% of the claw diseases.

It was surprising that a lot of researchers suggest that the etiological factors of DD, ID and IP are the same microorganisms, such as *Dichelobacter nodosus, Fusobacterium necroforun* and *Fusobacterium*, spp which first destroy the epidermis and allow the spirochetes from *Treponema* spp such as *T. phagedenis, T. vincentii*, and *T. denticola* to gain entrance into deeper tissues for developing the clinical sings of DD. Other bacterial species isolated from pathological material from tissues affected with DD, ID and IP are *Campylobacter* spp, *Staphylococcus aureus, Escherichia coli, Arcanobacterium pyogenes*, and *Prevotella* spp. Also, it was suggested that a virus plays an important role in the pathogenesis of the diseases.

The typical treatment strategy for DD, ID and IP is the application of antibiotics, antibacterial preparations and topical applications pads with antibiotics, antiseptics and astringent solutions. Intramuscular applications of penicillin or oxitetracelline during 3 days show good results for the treatment of IP but are not effective in the treatment of ID and DD.

For the treatment of IP, ID and DD the topical application of soluble oxytetracycline, lincomycin-spectinomycin, nitrofurazone or sulfa preparations, as well as a mixture of sulfamethazine powder and anhydrous copper sulfate can provide sufficient results. However, before the treatment the lesion must be thoroughly cleansed and the necrotic tissue has to be removed.

For preventive use a footbath with 7 to 10% copper or zinc sulfate or 3 to 5% formaldehyde solution can be used. Also footbaths with oxytetracycline or lincomycin-spectinomycin can be used. But, these solutions can contaminate the environment and are prohibited in some areas or countries. This method was accepted for control of IP and ID, but is less effective for the treatment of DD.

For treating DD, ID and IP a *Treponema* spp bacterin vaccine was developed in the US. It was shown that immunization with said vaccine could reduce clinical symptoms of DD in cattle. But, it was found in clinical trials that herd-specific pathogens including *Treponema* spp cannot provide sufficient protection against DD. Cows given the bacterin during the dry period had no reduction in lesions as compared with non-vaccinated control animals. The same results were obtained in Germany. It was concluded that treatment is not likely to be an effective therapeutic, control or prevention strategy for DD in the future. No respective commercial vaccine exists on the market.

A lot of investigations were done to induce protection against *F. necrophorum* by using different kinds of antigenic components. It was reported that cattle injected with *F. necrophorum* culture supernatant containing leukotoxin had a low incidence of foot rot caused by *F. necrophorum*. The stimulation with supernatant of a high leukotoxin producing strain of *F. necrophorum*, mixed with an adjuvant, resulted in a high antileukotoxin antibody titer when injected in steers and provided significant protection to experimentally induced liver abscesses. *F. necrophorum* bacterin was used as an agent for immunizing cattle and sheep against liver necrosis. Moreover, cells from culture of virulent *F. necrophorum* isolates were inactivated with 0.4% formalin. Mice immunized with said inactivated cells and with live *F. necrophorum* had no detectable bacteria in the liver, lung or spleen for up to 28 days. It was concluded that immunization of mice with formalin-killed *F. necrophorum* conferred protection against infection. Also, the injection of endotoxin with leukotoxic activity in immunized animals prevents the establishment of *F. necrophorum* infection.

In order to produce such a leukotoxoid vaccine, the *F. necrophorum* bacteria was cultured in a way to enhance the elaboration of leukotoxin in the supernatant. Bacterial growth and leukotoxin release was terminated, and a vaccine was prepared by inactivating at least the leukotoxin-containing supernatant. This was done by separating the leukotoxin-containing supernatant from the bacteria and subsequently by an inactivation with formalin, β-propiolactone, heat, radiation or any other known method of inactivation. Alternatively, the entire culture could be inactivated to form the vaccine.

Also known is another formalin-inactivated leukocidin-exotoxin obtained from the production strain *Fusobacterium necrophorum* "0-1" (Russian Research Institute of Experimental Veterinary Medicine) comprising 1-10% inactivated bacterial mass of said strain containing 7.0-7.7 billion cells per 1 cm, glycerol, a mixture of mineral oil "Markol-52", emulsifier taken in weight ratios of 1:(0.9-1.1), a suspension of live spores of splenic fever vaccine strain 55 (Russian Research Institute of Veterinary Virology and Microbiology) in saline, and adjuvant. Thus, immunization of the animals against *F. necrophorum* leukotoxin can prevent diseases associated with *F. necrophorum* infection, e.g., liver abscesses in cattle and sheep, and ID as well as IP in cattle.

A known vaccine for the prevention of necrobacteriosis in cattle comprises endotoxin and exotoxin antigens derived from pathogens necrobacteriosis (*F. necrophorum*), formalin inactivator, saline and an adjuvant based on mineral oil and lanolin. A known vaccine for necrobacteriosis farm animals comprises a complex of soluble antigens from strains *F. necrophorum* I and II serotypes, formalin, latex and adsorbent adjuvant. However, the known vaccines contain antigens of one type of pathogen and do not provide sufficient prophylactic activity for necrobacillosis, a diseases with anaerobic microorganisms and purulent wound microflora.

Also known are at least several inactivated commercial vaccines for the prophylaxis and treatment of ID and IP. Known is for example a polyvalent vaccine for the prevention of necrobacteriosis in cattle. Said vaccine contains formalin-inactivated antigens of *Fusobacterium necrophorum, Staph. aureus, Corynebac. pyogenes, Clostridium perfringens* type A toxoid *Cl. perfringens* type A, aluminium hydroxide adjuvant and immunopotentiator GMDP (N-acetilglukozamenil-(1-4)-N-acetimuromil-Z-alanin-D-isoglutamine). Also known is the vaccine "Nekovak" which comprises inactivated cultures of *Fusobacterium necrophorum* VGNKI N "Kp-1" DEP and/or *Fusobacterium necrophorum* VGNKI N "Tula" DEP, *Actinomyces* (Corybacterium) *pyogenes* VGNKI No. 4/2334 DEP, *Staphylococcus aureus* VGNKI No. 7315 DEP and *Clostridium perfringens* type A VGNKI No. 28 DEP. The vaccine also contains a toxoid from a strain of *Clostridium perfringens* type A VGNKI No. 28 DEP and aluminum hydroxide adjuvant. In addition, the vaccine contains a salt solution, such as saline.

All known vaccines often fail to elicit a sufficient immune response and to protect the animals against interdigital dermatitis and interdigital phlegmone. There are no effective vaccines against digital dermatitis.

Approaches concerning the use of inactivated dermatophytes as dermatomycosis vaccines are known in the art. For example, the active immunization against *Trichophyton purpureum* infection in rabbits with an inactivated suspension of *Trichophyton rubrum* hyphae is described. Also EP 393371 and WO 9307894 disclose inactivated dermatomycosis vaccines comprising dermatophytes of the genus *Trichophyton* and/or *Microsporum*. Moreover, mycoses vaccines are described in WO 98/15284 that comprise homogenized inactivated dermatophyte microconidia and inactivated homogenized yeast blastospores.

Dermatomycoses in animals are anthropozoonotic diseases of the skin and related tissue. Clinical symptoms are loss of hair in the affected area, hyperemia, scaling and asbestos-like scabs. Calves are more susceptible to ringworm infection than older animals. Dermatomycoses are often also characterized by localized infection of the skin. In cattle the lesions are most commonly found on the neck, head and consist of grey-white crusts raised on the skin. In addition, dermatomycoses may result in alopecia. Transmission of ringworm-causing organisms from infected animals to people has been reported. Dermatomycoses in animals carry a substantial socioeconomic impact. Diseased animals require prolonged treatment and can spread the infection to both animals and humans. Up till now, dermatomycoses have been treated using various types of medication applied locally to affected areas of the skin. These included a number of ointments, liniments, solutions and other substances containing fungicides and fungistatic agents. The disadvantages of such treatments are that they are not very effective, they require the adoption of quarantine measures and disinfection of areas where animals have been kept (rearing pens, vivaria, farms, zoos, circuses, etc.). Moreover, they require substantial funds to be spent on drug preparations and veterinary treatment and they pose difficulties in immobilizing the animals (for wild animals held in captivity). Inactivated vaccines were developed to treat trichophytosis in cattle, dermatophytosis in horses, cats and dogs as e.g. described in WO 93/07894 and live vaccines to treat furbearing animals and rabbits (see USSR Patent No. 835446), camels (see USSR Patent No. 1190574) and others. A vaccine had also been developed for the prevention and treatment of mycosis in mammals (see WO 98/15284).

Thus, the object of the present invention is the provision of new compositions for use in a method of treating and/or preventing hoof- and claw diseases in animals. It is a further object of the present invention to provide compositions fur use in a method of treating and/or preventing digital and/or interdigital dermatitis and/or interdigital phlegmone in animals, in particular in bovidae and pigs. It is a further object of the present invention to provide a new *Trichophyton verrucosum* strain. It is a further object of the present invention to provide compositions fur use in a method of treating and/or preventing dermatophytosis.

These objects are solved by the subject matter defined in the claims.

The use of the word "a" or "an" when used in conjunction with the term "comprising" in the claims and/or the description may mean "one," but it is also consistent with the meaning of "one or more," "at least one," and "one or more than one."

The term "about" means that the value stated, plus or minus 5% of the stated value, or the standard error for measurements of the given value, are contemplated.

The term "comprising" as used herein shall not be construed as being limited to the meaning "consisting of" (i.e. excluding the presence of additional other matter). Rather, "comprising" implies that optionally additional matter may be present. The term "comprising" encompasses as particularly envisioned embodiments falling within its scope "consisting of" (i.e. excluding the presence of additional other matter) and "comprising but not consisting of" (i.e. requiring the presence of additional other matter), with the former being more preferred.

The term "hoof- and claw disease" as used herein refers in particular to infectious hoof- and claw diseases in bovidae and/or pigs. Said diseases are in particular caused by bacteria, fungi and/or viruses. In particular the term "hoof- and claw diseases" refers to digital dermatitis, interdigital dermatitis and interdigital phlegmone.

The term "bovidae" as used herein refers in particular to cloven-hoofed, ruminant mammals including includes bison, African buffalo, water buffalo, antelopes, gazelles, sheep, goats, muskoxen, and cattle.

The term "lameness" as used herein refers in particular to lameness as a result of an infection and damage to tissue. In particular, the term "lameness" refers to lameness due to hoof and claw diseases, more particularly due to digital dermatis, interdigital dermatitis and interdigital phlegmone.

The term "chitosan" as used herein refers to a copolymer of 2-amino-2-deoxy-D-Glucopyranose and 2-acetamido-2-deoxy-D-glucopyranose, where the degree of deacetylation is more than 50%, preferably more than 60%, 70%, 80% or 90%. Chitosan may be chemically derived from chitin which is a poly-1,4-β-N-acetyl-D-glucosamine, more particularly a N-acetyl-1,4-β-D-glucopyranosamine by deacetylation. Typical chitosan preparations have varying molecular weights depending on the method of manufacture.

It was now surprisingly found, that vaccines comprising antigenic material of keratinophilic fungi or yeasts confer good resistance and prophylactic and curing effect against digital dermatitis, interdigital dermatitis and interdigital phlegmon in animals. In particular, it was surprisingly found that vaccines comprising homogenised inactivated dermatophyte microconidia and/or inactivated homogenized yeast blastospores confer good resistance and prophylactic and curing effect against digital dermatitis, interdigital dermatitis and interdigital phlegmon in animals.

The present invention relates to a composition comprising antigenic material of keratinophilic fungi or keratinophilic yeasts for use in a method of treating and/or preventing hoof- and claw diseases in animals. Preferably, the animals are mammals, more preferably bovidae and/or pigs, most preferably cattle.

The antigenic material of keratinophilic fungi or yeasts may be derived from any parts of keratinophilic fungi or yeasts comprising antigens such as from the mycelium, artrospores, dermatophyte microconidia, yeast blastospores or others. The antigens are preferably polysaccharides and/or glycopeptides. Preferably, the antigenic material of keratinophilic fungi or yeasts is selected from the group consisting of: homogenised inactivated dermatophyte microconidia, homogenised inactivated yeast blastospores, antigenic material of yeast blastospores and antigenic material of dermatophyte microconidia. Thus, the present invention more particularly relates to a composition comprising homogenised inactivated dermatophyte microconidia and/or homogenised inactivated yeast blastospores and/or antigenic material of yeast blastospores and/or dermatophyte microconidia.

In particular, the hoof- and claw diseases result in lameness. More particularly, the hoof- and claw diseases are digital dermatitis and/or interdigital dermatitis and/or interdigital phlegmone. The hoof- and claw diseases and digital dermatitis, interdigital dermatitis, interdigital phlegmone, respectively, may be caused by *Dichelobacter nodosus, Fusobacterium necroforun, Fusobacterium* spp, *Treponema* spp such as *T. phagedenis, T. vincentii,* and *T. denticola, Campylobacter* spp, *Staphylococcus aureus, Escherichia coli, Arcanobacterium pyogenes,* and *Prevotella* spp. and/or a virus.

The antigenic material of keratinophilic yeasts, in particular the yeast blastospores, of the composition for use of the present invention belong preferably to the genus *Candida* and more preferably to the species *Candida albicans*. The antigenic material of keratinophilic dermatophyte, in particular the dermatophyte microconidia, belong preferably to the genera *Trichophyton* and/or *Microsporum*. More preferably, the dermatophyte microconidia belong to the species *Trichophyton verrucosum, Trichophyton mentagrophytes, Trichophyton equinum, Trichophyton sarkisovii, Trichophyton rubrum, Trichophyton mentagrophytes, Microsporum canis* and/or *Microsporum gypseum*. In particular, the species *Microsporum canis* can be *Microsporum canis* var. *obesum* and/or *Microsporum canis* var. *distortum*.

In a preferred embodiment of the present invention the yeast blastospores and the dermatophyte microconidia are obtained from strains of the above mentioned species which have been obtained by directed selection based on spore production and/or attenuation. It is highly preferred to use a strain which grow faster in nutrient medium, produces more microconidia and blastospores, respectively, has a lower virulence and/or no adverse reactions after its intramuscular application in comparison to any epizootic strain from which it is derived. Examples of such strains are the strains *Trichophyton mentagrophytes* DSM-7279, *Trichophyton verrucosum* DSM-28406, *Trichophyton rubrum* DSM-9469, *Trichophyton rubrum* DSM-9470, *Trichophyton rubrum* DSM-9471, *Trichophyton rubrum* DSM-9472, *Candida albicans* DSM-9456, *Candida albicans* DSM-9457, *Candida albicans* DSM-9458, and *Candida albicans* DSM-9459. Thus, in especially preferred embodiments of the present invention the yeast blastospores and the dermatophyte microconidia are obtained from strains *Trichophyton mentagrophytes* DSM-7279, *Trichophyton verrucosum* DSM-28406, *Trichophyton rubrum* DSM-9469, *Trichophyton rubrum* DSM-9470, *Trichophyton rubrum* DSM-9471, *Trichophyton rubrum* DSM-9472, *Candida albicans* DSM-9456, *Candida albicans* DSM-9457, *Candida albicans* DSM-9458, and *Candida albicans* DSM-9459.

The strains *Trichophyton rubrum* DSM-9469, *Trichophyton rubrum* DSM-9470, *Trichophyton rubrum* DSM-9471, *Trichophyton rubrum* DSM-9472, *Candida albicans* DSM-9456, *Candida albicans* DSM-9457, *Candida albicans* DSM-9458, and *Candida albicans* DSM-9459 have been deposited according to the Budapest Treaty at the "Deutsche Sammlung von Mikroorganismen und Zellkulturen" (DSM), Mascheroder Weg 1B, W-38124 Braunschweig, Germany (which current name and address is "Leibniz-Institut DSMZ-Deutsche Sammlung von Mikroorganismen und Zellkulturen GmbH" (DMSZ), Inhoffenstraße 7B, 38124 Braunschweig, GERMANY) on 5 Oct. 1994 by the Basotherm GmbH, Eichendorffweg 5, 88396 Biberach an der Riss. The current depositors of said strains are the applicants, namely Dr. Igor Polyakov and Dr.sc.Dr. Liudmila Ivanova, Eberhardtstr. 40, 89073 Ulm.

*Trichophyton Rubrum*, No. DSM-9469

The strain was deposited at the DSM on May 10, 1994 under Serial No. DSM-9469. The strain was obtained by directed selection based on spore production and attenuation of the epizootic strain No. 533, which was identified on a skin of man in 1985. The strain was identified using the "Rebell-Taplin" key (Rebell, G., Taplin, D.: Dermatophytes, their recognition and identification, 3rd Print, University of Miami Press. Coral Gables, Fla., USA, 1978). The biological properties of the strain are described in Table A. Strain No. DSM-9469 differs from the epidemic strain in its faster growth in nutrient medium, an enormous production of microconidiae and lower virulence.

TABLE A

| Properties and characteristics of the strains | Strain No. DSM-9469 | Epidemic Strain No. 533 |
|---|---|---|
| Description of the culture | Mature 15-day colony on agar Sabouraud: white, velvety, flat, margin of the colony fringed, under surface yellow, in centre deep purple, diameter of colony 60-63 mm | 20-day colony on agar Sabouraud: white, downy, elevated, margin of colony regular, under surface purple, diameter of colony 30-35 mm |
| Morphological characteristics | Mature 15-day culture with septate branching hyphae 1-3 μm wide, numerous obovate oval microconidia measuring 2-3 × 3-5 μm, macroconidia long clavate pencil-shaped with 4-5 cross walls measuring 4-6 × 15-40 μm. | 20-day culture with septate branching hyphae 1-3 μm wide, microconidia clavate to round in small open clusters and along the hyphae measuring 2-3 × 3-6 μm; macroconidia are rare, long and pencil-shaped with 3-5 cross walls measuring 4-7 × 15-50 μm. |
| Pathogenic characteristics | The strain is weakly virulent. 9-10 days after application of a dose of 500-600 thousand cells of fungal material per $cm^2$ on scarified skin of guinea pigs, scales are formed. Spontaneous recovery after 18-20 days. | The strain is virulent. 9-10 days after application of a dose of 500-600 thousand cells of fungal material per $cm^2$ on scarified skin of guinea pigs, thin necrotic scabs are formed. Spontaneous recovery after 25-30 days. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of guinea pigs with inactivated antigen from cultures (repeated not less than 5 times): establishes immunity | Results of immunisation of a group of guinea pigs with inactivated antigen from cultures (repeated not less than 5 times): establishes immunity |

*Trichophyton Rubrum*, No. DSM-9470

The strain was deposited at the DSM on May 10, 1994 under Serial No. DSM-9470. The strain was obtained by directed selection based on spore production and attenuation of the epizootic strain No. 535, which was identified on a skin of man in 1990. The strain was identified using the "Rebell-Taplin" key (Rebell, G., Taplin, D.: Dermatophytes, their recognition and identification, 3rd Print, University of Miami Press. Coral Gables, Fla., USA, 1978). The biological properties of the strain are described in Table B. Strain No. DSM-9470 differs from the epidemic strain in its faster growth in nutrient medium, an enormous production of microconidiae and lower virulence.

TABLE B

| Properties and characteristics of the strains | Strain No. DSM-9470 | Epidemic Strain No. 535 |
|---|---|---|
| Description of the culture | Mature 15-day colony on agar Sabouraud: white velvety-fluffy in centre, folded, margin of colony regular, under surface colourless or rose, diameter of colony 25-30 mm | 20-day colony on agar Sabouraud: white, fluffy, margin of colony regular, under surface yellow, 20 mm in diameter |

TABLE B-continued

| Properties and characteristics of the strains | Strain No. DSM-9470 | Epidemic Strain No. 535 |
|---|---|---|
| Morphological characteristics | Mature 15-day culture with septate branching hyphae 1-3 μm wide, round oval puriform microconidia measuring 2-3 × 3-7 μm. | 20-day culture with septate branching hyphae 1-3 μm wide, microconidia clavate to round in small open clusters and along the hyphae measuring 2-3 × 3-6 μm; macroconidia are absent. |
| Pathogenic characteristics | The strain is weakly virulent. 9-10 days after application of a dose of 500-600 thousand cells of fungal material per cm$^2$ on scarified skin of guinea pigs, necrotic scabs are formed. Spontaneous recovery after 22-25 days. | The strain is virulent. 9-10 days after application of a dose of 500-600 thousand cells of fungal material per cm$^2$ on scarified skin of guinea pigs, thin necrotic scabs are formed. Spontaneous recovery after 25-30 days. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of guinea pigs with inactivated antigen from cultures (repeated not less than 5 times): establishes immunity | Results of immunisation of a group of guinea pigs with inactivated antigen from cultures (repeated not less than 5 times): establishes immunity |

*Trichophyton Rubrum*, No. DSM-9471

The strain was deposited at the DSM on May 10, 1994 under Serial No. DSM-9471. The strain was obtained by directed selection based on spore production and attenuation of the epizootic strain No. 620, which was identified on a nail of man in 1989. The strain was identified using the "Rebell-Taplin" key (Rebell, G., Taplin, D.: Dermatophytes, their recognition and identification, 3rd Print, University of Miami Press. Coral Gables, Fla., USA, 1978). The biological properties of the strain are described in Table C. Strain No. DSM-9471 differs from the epidemic strain in its faster growth in nutrient medium, an enormous production of microconidiae and lower virulence.

TABLE C

| Properties and characteristics of the strains | Strain No. DSM-9471 | Epidemic Strain No. 620 |
|---|---|---|
| Description of the culture | Mature 15-day colony on agar Sabouraud: white, velvety, elevated, margin of colony regular, under surface yellow, in centre deep purple, diameter of colony 32-35 mm | 20-day colony on agar Sabouraud: white, downy, elevated, margin of colony regular, under surface purple, diameter of colony 20-25 mm |
| Morphological characteristics | Mature 15-day culture with septate branching hyphae 1-3 μm wide, round oval puriform microconidia measuring 2-3 × 3-7 μm. | 20-day culture with septate branching hyphae 1-3 μm wide, microconidia clavate to round in small open clusters and along the hyphae measuring 2-3 × 3-6 μm; macroconidia are rare, long and pencil-shaped with 3-5 cross walls measuring 4-7 × 15-50 μm. |
| Pathogenic characteristics | The strain is weakly virulent. 9-10 days after application of a dose of 500-600 thousand cells of fungal materials per cm$^2$ on scarified skin of guinea pigs, scales are formed. Spontaneous recovery after 18-20 days. | The strain is virulent. 9-10 days after application of a dose of 500-600 thousand cells of fungal materials per cm$^2$ on scarified skin of guinea pigs, thin necrotic scabs are formed. Spontaneous recovery after 25-30 days. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |

TABLE C-continued

| Properties and characteristics of the strains | Strain No. DSM-9471 | Epidemic Strain No. 620 |
|---|---|---|
| Immunogenic response | Results of immunisation of a group of guinea pigs with inactivated antigen from cultures (repeated not less than 5 times): establishes immunity | Results of immunisation of a group of guinea pigs with inactivated antigen from cultures (repeated not less than 5 times): establishes immunity |

*Trichophyton Rubrum*, No. DSM-9472

The strain was deposited at the DSM on May 10, 1994 under Serial No. DSM-9472. The strain was obtained by directed selection based on spore production and attenuation of the epizootic strain No. 754, which was identified on a nail of man in 1990. The strain was identified using the "Rebell-Taplin" key (Rebell, G., Taplin, D.: Dermatophytes, their recognition and identification, 3rd Print, University of Miami Press. Coral Gables, Fla., USA, 1978). The biological properties of the strain are described in Table D. Strain No. DSM-9472 differs from the epidemic strain in its faster growth in nutrient medium, an enormous production of microconidiae and lower virulence.

*Candida Albicans*, No. DSM-9456

The strain was deposited at the DSM on May 10, 1994 under Serial No. DSM-9456. The strain was obtained by directed selection based on stabilisation of cultural-morphological characteristics and attenuation of epidemic strain No. 008-L, which was identified on man in 1990. The strain was identified using the Lodder's key (Lodder, J: The yeast: A Taxonomic Study. North-Holland Publ. Co., Amsterdam-London (1970). The biological properties of the strain are described in Table E. Strain No. DSM-9456 differs from the epidemic strain in its faster growth in nutrient medium, stabile biological properties, an enormous production of biomass and lower virulence.

TABLE D

| Properties and characteristics of the strains | Strain No. DSM-9472 | Epidemic Strain No. 754 |
|---|---|---|
| Description of the culture | Mature 15-day colony on agar Sabouraud: white, velvety, in centre folded, margin of colony regular, under surface yellow in centre purple, diameter of colony 35-40 mm | 20-day colony on agar Sabouraud: white-rose, downy, margin of colony regular, under surface purple, diameter of colony 20-25 mm |
| Morphological characteristics | Mature 15-day culture with septate branching hyphae 1-3 µm wide, round oval puriform microconidia measuring 2-3 × 3-7 µm. | 20-day culture with septate branching hyphae 1-3 µm wide, microconidia clavate to round in small open clusters and along the hyphae measuring 2-3 × 3-6 µm; macroconidia are rare, long and pencil-shaped with 3-5 cross walls measuring 4-7 × 15-50 µm. |
| Pathogenic characteristics | The strain is weakly virulent. 9-10 days after application of a dose of 500-600 thousand cells of fungal materials per $cm^2$ on scarified skin of guinea pigs, scales are formed. Spontaneous recovery after 18-20 days. | The strain is virulent. 9-10 days after application of a dose of 500-600 thousand cells of fungal materials per $cm^2$ on scarified skin of guinea pigs, thin necrotic scabs are formed. Spontaneous recovery after 25-30 days. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of guinea pigs with inactivated antigen from cultures (repeated not less than 5 times): establishes immunity | Results of immunisation of a group of guinea pigs with inactivated antigen from cultures (repeated not less than 5 times): establishes immunity |

TABLE E

| Properties and characteristics of the strains | Strain No. DSM-9456 | Epidemic Strain No. 008-L |
| --- | --- | --- |
| Description of the culture | 10-day single-spore colony on agar Sabouraud: cream smooth and pasty glistening, elevated, margin of colony regular, diameter of colony 20-30 mm | 10-day single-spore colony on agar Sabouraud: cream soft and smooth with feathery offshots at the edges, diameter of colony 10-15 mm |
| Morphological characteristics | 10-day culture with spherical oval blastospores measuring 3.5-6 × 6-10 μm, chiamidospores 12-15 μm wide, pseudohyphae 5-8 μm wide, hyphae 1.5-3 μm wide | 10-day single-spore culture on agar Sabouraud with spherical oval budding blastospores measuring 3-5 × 5-8 μm, chlamidospores 10-15 μm diameter, pseudohyphae 5-8 μm wide, hyphae 1.5-3 μm wide. |
| Pathogenic characteristics | The strain is weakly virulent. 30 days after intraperitoneal injection of a dose of 10-100 million fungal cells to white mice, granuloma in abdominal organs of 50% of animals are formed. Lethal effect was not observed. | The strain is weakly virulent. 30 days after intraperitoneal injection of a dose of 10-100 million fungal cells to white mice, granuloma in abdominal organs of 80-100% of animals are formed. Lethal effect in 50-70% was observed. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of white mice with inactivated antigen from cultures (repeated not less than 10 times): establishes immunity | Results of immunisation of a group of white mice with inactivated antigen from cultures (repeated not less than 10 times): establishes immunity |

*Candida Albicans*, No. DSM-9457 The strain was deposited at the DSM on May 10, 1994 under Serial No. DSM-9457. The strain was obtained by directed selection based on stabilisation of cultural-morphological characteristics and attenuation of epidemic strain No. 012, which was identified on man in 1992. The strain was identified using the Lodder's key (Lodder, J: The yeast: A Taxonomic Study. North-Holland Publ. Co., Amsterdam-London (1970). The biological properties of the strain are described in Table F. Strain No. DSM-9457 differs from the epidemic strain in its faster growth in nutrient medium, stabile biological properties, an enormous production of biomass and lower virulence.

TABLE F

| Properties and characteristics of the strains | Strain No. DSM-9457 | Epidemic Strain No. 012 |
| --- | --- | --- |
| Description of the culture | 10-day single-spore colony on agar Sabouraud: cream rough elevated, margin of colony lobulated, diameter of colony 20-23 mm | 10-day single-spore colony on agar Sabouraud: cream rough elevated, margin of colony fringed and lobulated, diameter of colony 15-20 mm |
| Morphological characteristics | 10-day single-spore culture with spherical oval blastospores measuring 3.5-5 × 5-10 μm, chlamidospores 12-15 μm wide, pseudohyphae 4-7 μm wide, hyphae 2-3 μm wide | 10-day single-spore culture on agar Sabouraud with spherical oval budding blastospores measuring 3-5 × 5-8 μm, chlamidospores 10-15 μm diameter, pseudohyphae 5-8 μm wide, hyphae-1.5-3 μm wide |
| Pathogenic characteristics | The strain is weakly virulent. 30 days after intraperitoneal injection of a dose of 10-100 million fungal cells to white mice, granuloma in abdominal organs in 30% of animals are formed. Lethal effect was not observed. | The strain is weakly virulent. 30 days after intraperitoneal injection by dose of 10-100 million fungal cells to white mice, granuloma in abdominal organs of 50% of animals are formed. Lethal effect not more 50% were observed. |

TABLE F-continued

| Properties and characteristics of the strains | Strain No. DSM-9457 | Epidemic Strain No. 012 |
| --- | --- | --- |
| Reaction response | Result of intramuscular injection of inactivated corpuscular antigens from cultures: no observed changes in clinical state of animals | Result of intramuscular injection of inactivated corpuscular antigens from cultures: no observed changes in clinical state of animals |
| Immunogenic response | Results of immunisation of a group of white mice with inactivated antigen from cultures (repeated not less than 10 times): establishes immunity | Results of immunisation of a group of white mice with inactivated antigen from cultures (repeated not less than 10 times): establishes immunity |

*Candida Albicans*, No. DSM-9458

The strain was deposited at the DSM on May 10, 1994 under Serial No. DSM-9458. The strain was obtained by directed selection based on stabilisation of cultural-morphological characteristics and attenuation of epidemic strain No. 047, which was identified on man in 1989. The strain was identified using the Lodder's key (Lodder, J: The yeast: A Taxonomic Study. North-Holland Publ. Co., Amsterdam-London (1970). The biological properties of the strain are described in Table G. Strain No. DSM-9458 differs from the epidemic strain in its faster growth in nutrient medium, stabile biological properties, an enormous production of biomass and lower virulence.

*Candida Albicans*, No. DSM-9459

The strain was deposited at the DSM on May 10, 1994 under Serial No. DSM-9459. The strain was obtained by directed selection based on stabilisation of cultural-morphological characteristics and attenuation of epidemic strain No. 158, which was identified on man in 1990. The strain was identified using the Lodder's key (Lodder, J: The yeast: A Taxonomic Study. North-Holland Publ. Co., Amsterdam-London (1970). The biological properties of the strain are described in Table H. Strain No. DSM-9459 differs from the epidemic strain in its faster growth in nutrient medium, stable biological properties, an enormous production of biomass and lower virulence.

TABLE G

| Properties and characteristics of the strains | Strain No. DSM-9458 | Epidemic Strain No. 047 |
| --- | --- | --- |
| Description of the culture | 10-day single-spore colony on agar Sabouraud: cream smooth and pasty glistening, elevated, margin of colony regular, diameter of colony 16-18 mm | 10-day single-spore colony on agar Sabouraud: cream soft and smooth with feathery offshots at the edges, diameter of colony 10-15 mm |
| Morphological characteristics | 10-day culture with spherical oval blastospores measuring 3.6-6 × 6-11 µm, chlamidospores 12-15 µm wide, pseudohyphae 4-8 µm wide, hyphae 1.5-3 µm wide | 10-day single-spore culture on agar Sabouraud with spherical oval budding blastospores measuring 3-5 × 5-8 µm, chlamidospores 10-15 µm diameter, pseudohyphae 5-8 µm wide, hyphae 1.5-3 µm wide. |
| Pathogenic characteristics | The strain is weakly virulent. 30 days after intraperitoneal injection of a dose of 10-100 million fungal cells to white mice, granuloma in abdominal organs of 50-100% of animals are formed. Lethal effect in 50% were observed. | The strain is weakly virulent. 30 days after intraperitoneal injection by dose of 10-100 million fungal cells to white mice, granuloma in abdominal organs of 80-100% of animals are formed. Lethal effect in 70-100% were observed. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of white mice with inactivated antigen from cultures (repeated not less than 10 times): establishes immunity | Results of immunisation of a group of white mice with inactivated antigen from cultures (repeated not less than 10 times): establishes immunity |

TABLE H

| Properties and characteristics of the strains | Strain No. DSM-9459 | Epidemic Strain No. 158 |
|---|---|---|
| Description of the culture | 10-day single-spore colony on agar Sabouraud: cream smooth pasty glistening, elevated, margin of colony regular, diameter of colony 16-18 mm | 10-day single-spore colony on agar Sabouraud: cream smooth pasty, margin of colony lobulated and with feathery offshots at the edges, diameter of colony 10-15 mm |
| Morphological characteristics | 10-day culture with spherical oval blastospores measuring 3.6-6 × 6-11 µm, chlamidospores 12-15 µm wide, pseudohyphae 4-8 µm wide, hyphae 1.5-3 µm wide | 10-day single-spore culture on agar Sabouraud with spherical oval budding blastospores measuring 3-5 × 5-8 µm, chlamidospores 10-15 µm diameter, pseudohyphae 5-8 µm wide, hyphae 1.5-3 µm wide. |
| Pathogenic characteristics | The strain is weakly virulent. 30 days after intraperitoneal injection by dose of 10-100 million fungal cells to white mice, granuloma in abdominal organs of 40% of animals are formed. Lethal effect was not observed. | The strain is weakly virulent. 30 days after intraperitoneal injection by dose of 10-100 million fungal cells to white mice, granuloma in abdominal organs of 50% of animals are formed. Lethal effect in 20-50% was observed. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of white mice with inactivated antigen from cultures (repeated not less than 10 times): establishes immunity | Results of immunisation of a group of white mice with inactivated antigen from cultures (repeated not less than 10 times): establishes immunity |

Strain *Trichophyton mentagrophytes* DSM-7279 has been deposited according to the Budapest Treaty at the "Deutsche Sammlung von Mikroorganismen and Zellkulturen" (DSM), Mascheroder Weg 1B, W-38124 Braunschweig, Germany (which current name and address is "Leibniz-Institut DSMZ-Deutsche Sammlung von Mikroorganismen und Zellkulturen GmbH" (DMSZ), Inhoffenstraβe 7B, 38124 Braunschweig, GERMANY) on 1 Oct. 1992 by Boehringer Ingelheim Vetmedica GmbH, 6507 Ingelheim am Rhein (which current address is Boehringer Ingelheim Vetmedica GmbH, 55216 Ingelheim am Rhein). The current depositors of said strain are the applicants, namely Dr. Igor Polyakov and Dr.sc.Dr. Liudmila Ivanova, Eberhardtstr. 40, 89073 Ulm.

*Trichophyton Mentagrophytes* No. VKPGF-930/1032, No. DSM-7279

The strain was deposited at the DSM on 1 Oct. 1992 under Serial No. DSM-7279. The strain was obtained by directed selection based on spore production and attenuation of the epizootic Strain No. 1032, which was found on a horse in 1985. The strain was identified as described above Rebel, Taplin, loc. cit. and Kashkin, loc. cit.). The biological properties are described in Table I. Strain No. VKPGF-930/1032, DSM-7279, differs from the epizootic strain by its faster growth in nutrient medium, the enormous production of microconidia, its lower virulence and the absence of any reaction with its antigens.

*Trichophyton verrucosum*, No. DSM-28406

The strain *Trichophyton verrucosum* BINO 348 was deposited by the Binomed GmbH (Einsteinstraβe 59, 89077 Ulm) according to the Budapest Treaty at the—Leibniz-Institut DSMZ—Deutsche Sammlung von Microorganismen und Zellkulturen GmbH, Inhoffenstraβe 7B, 38124 Braunschweig, Germany under Serial No. DSM-28406 on 12 Feb. 2014. The depositor has authorized the applicants to refer to the deposited biological material in the application and has given his unreserved and irrevocable consent to the deposited material being made available to the public in accordance with Rule 31 EPC. The strain was obtained by directed selection based on spore production and attenuation of epizootic strain Nr. 348, which was isolated from cattle in 1997. The strain was identified using the Rebell-Taplin key (Rebell, G., Taplin, D.: Dermatophytes, their recognition and identification, 1978) and according to Kashkin, P. N. et. al. (opredelitel patogennykh, toksigenykh vrednykh dlya cheloveka gribov, 1979). The biological properties of the strain are described in Table J. Strain BINO 348-DSM 28406 differs from the epizootic strain in its faster growth in nutrient medium, the enormous production of microconidia, lower virulence and the absence of any adverse reactions after intramuscular application of antigens.

TABLE I

| Properties and characteristics of strain | Strain No. VKPGF-930/1032 | Epizootic Strain No. 1032 |
|---|---|---|
| Description of culture | Mature 10-15 day colony in agar/wort; cream, velvety/powdered, flat with slight flat elevation in center, narrow | Mature 25-30 day colony in agar/wort; white, flat, narrow, growing margin, undersurface reddish-brown, colony |

TABLE I-continued

| Properties and characteristics of strain | Strain No. VKPGF-930/1032 | Epizootic Strain No. 1032 |
|---|---|---|
| Morphological characteristics | growing margin, fringed, undersurface light brown, colony diameter 25-30 mm Septate, branching hyphae 1-3 µm wide, numerous pyriform, oval microconidia measuring 1 to 3 × 2 to 6 µm, no macroconidia | diameter: 15-20 mm Septate, branching straight and spiral hyphae 1-3 µm wide, round, flattened pyriform microconidia measuring 1 to 3 × 2 to 6 µm, few elongate-oval macroconidia with 2-5 septates, measuring 2 to 6 × 15 to 25 µm |
| Pathogenic characteristics 9 to 10 days after application of a dose of 500-600 thousand cells of fungal matter per cm$^2$ to the scarified skin of a rabbit | Necrotic scabs | Dense, asbestos-like scabs |
| Spontaneous recovery after | 22-25 days | 30-35 days |
| Reaction response Results of subcutaneous and intramuscular injection of inactivated corpuscular antigens from cultures | No observed changes in clinical state | Inflammation at point of injection, edema |
| Antigen response 20 to 25 days after injecting rabbits with corpuscular antigens, antibody titers observed in blood serum | | |
| By PHR | 1:320 to 1:640 | 1:320 to 1:640 |
| By ELISA | 1:400 to 1:1600 | 1:400 to 1:1600 |
| Immunogenic response Immunization of a group of rabbits with inactivated antigens from cultures (repeated at least 5 times) | Establishes immunity | Establishes immunity |

TABLE J

| Properties and characteristics of the strains | Strain No. DSM-28406 | Epidemic Strain No. 348 |
|---|---|---|
| Description of the culture | 20-day colony on Malt Extract Agar: white or light-yellow, velvety, furrowed, diameter of colony 15-20 mm | 25-30-day colony in Malt Extract Agar: light-yellow cream, velvety, folded, undersurface colorless, diameter of colony 10-12 mm |
| Morphological characteristics | Mature 20-day culture with numerous oval, pyriform microconidia measuring 1.5-3 × 3-5 µm. | Mature 25-30 day culture with septate branching mycelium, few oval, pyriform microconidia 1 to 3 µm × 3 to 6 µm, macroconidia with 2 to 6 septates, few arthrospores and chlamydospores 9-11 µm. |
| Pathogenic characteristics | The strain is weakly virulent. 9-10 days after application of a dose of 500-600 thousand cells of fungal material per cm$^2$ on scarified skin of guinea pigs, scales are formed. Spontaneous recovery after 15-20 days. | The strain is virulent. 9-10 days after application of a dose of 500-600 thousand cells of fungal material per cm$^2$ on scarified skin of guinea pigs, thin necrotic scabs are formed. Spontaneous recovery after 25-30 days. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of guinea pigs with inactivated antigen from cultures (repeated not less than 5 times): establishes immunity against dermatophytos cause by T. verrucosum | Results of immunisation of a group of guinea pigs with inactivated antigen from cultures (repeated not less than 5 times): establishes immunity against dermatophytos cause by T. verrucosum |

In a preferred embodiment of the composition for use of the present invention the composition comprises homogenised inactivated dermatophyte microconidia of one microconidia or a mixture of microconidia of two, three, four, five, six, seven, eight, nine or ten of the above listed strains of dermatophytes. In a further preferred embodiment the composition comprises a mixture of homogenised inactivated dermatophyte microconidia of one, two, three, four, five, six, seven, eight, nine or ten of the above listed dermatophytes and homogenised inactivated yeast blastospores of one, two, three, or four of the above listed yeasts. In a further preferred embodiment the composition comprises homogenised inactivated dermatophyte microconidia of one or a mixture of two, three, or four of the above listed yeasts. The compositions may additionally comprise antigenic material of dermatophyte microconidia and/or antigenic material of yeast blastospores as described herein. Alternatively or in addition, the compositions may additionally comprise chitosan modified by an organic carboxylic acid, or a salt thereof.

In a further preferred embodiment the composition comprises antigenic material of one dermatophyte microconidia or a mixture of antigenic material of dermatophyte microconidia of two, three, four, five, six, seven, eight, nine or ten of the above listed strains of dermatophyte. In a further preferred embodiment the composition comprises a mixture of antigenic material of dermatophyte microconidia of one, two, three, four, five, six, seven, eight, nine or ten of the above listed dermatophytes and antigenic material of yeast blastospores of one, two, three, or four of the above listed yeasts. In a further preferred embodiment the composition comprises antigenic material of yeast blastospores of one or a mixture of two, three, or four of the above listed yeasts. The compositions may additionally comprise homogenised inactivated dermatophyte microconidia of one, two, three, four, five, six, seven, eight, nine or ten of the above listed dermatophytes and/or homogenised inactivated yeast blastospores of one, two, three, or four of the above listed yeasts. Alternatively or in addition, the compositions may additionally comprise chitosan modified by an organic carboxylic acid, or a salt thereof.

In a preferred embodiment the composition for use of the present invention comprises a mixture of homogenised inactivated dermatophyte microconidia of *Trichophyton mentagrophytes, Trichophyton verrucosum, Trichophyton equinum, Trichophyton sarkisovii, Microsporum canis, Microsporum canis* var. *obesum, Microsporum canis* var. *distortum* and *Microsporum gypseum*. For example, the vaccine Polivac-TM (manufacturer: "Vetbiochim" LLC, Moscow; Distributor: "Prostore" LLC, Moscow) is in accordance with this embodiment and can be used as a composition for use of the present invention. Polivac-TM is a vaccine designed for animals such as cats, dogs, horses and others. The composition may additionally comprise antigenic material as described herein and/or chitosan modified by an organic carboxylic acid, or a salt thereof.

In a further preferred embodiment the composition for use of the present invention comprises a mixture of homogenised inactivated dermatophyte microconidia of *Trichophyton mentagrophytes, Trichophyton verrucosum* and *Trichophyton sarkisovii*. For example, the vaccine Polivac-T (manufacturer: "Vetbiochim" LLC, Moscow; Distributor: "Prostore" LLC, Moscow) is in accordance with this embodiment and can be used as a composition for use of the present invention. Polivac-T is a vaccine specifically designed for cattle. The composition may additionally comprise antigenic material as described herein and/or chitosan modified by an organic carboxylic acid, or a salt thereof. In a further preferred embodiment the composition for use of the present invention comprises a mixture of homogenised inactivated dermatophyte microconidia of *Trichophyton mentagrophytes, Trichophyton verrucosum* and *Trichophyton sarkisovii* and homogenized inactivated yeast blastospores of *Candida albicans*. The composition may additionally comprise antigenic material as described herein and/or chitosan modified by an organic carboxylic acid, or a salt thereof.

In a further preferred embodiment the composition for use of the present invention comprises homogenised inactivated dermatophyte microconidia of *Trichophyton mentagrophytes*, in particular *Trichophyton mentagrophytes* DSM-7279. The composition may additionally comprise antigenic material as described herein and/or chitosan modified by an organic carboxylic acid, or a salt thereof.

In a further preferred embodiment the composition for use of the present invention comprises homogenised inactivated dermatophyte microconidia of *Trichophyton verrucosum*, in particular *Trichophyton verrucosum* DSM-28406. The composition may additionally comprise antigenic material as described herein and/or chitosan modified by an organic carboxylic acid, or a salt thereof.

In a further preferred embodiment the composition for use of the present invention comprises a mixture of homogenised inactivated dermatophyte microconidia of *Trichophyton verrucosum*, in particular of *Trichophyton verrucosum* DSM-28406 and homogenized inactivated yeast blastospores of *Candida albicans*, in particular of *Candida albicans* DSM-9456. The composition may additionally comprise antigenic material as described herein chitosan modified by an organic carboxylic acid, or a salt thereof.

In a further preferred embodiment the composition for use of the present invention comprises a mixture of homogenised inactivated dermatophyte microconidia of *Trichophyton mentagrophytes, Trichophyton verrucosum* and *Trichophyton sarkisovii*. For example, a variation of the vaccine Polivac-TM comprising in comparision to the classical Polivac-TM no *Trichophyton equinum* and *Microsporum* strains (manufacturer: "Vetbiochim" LLC, Moscow; Distributor: "Prostore" LLC, Moscow) is in accordance with this embodiment and can be used as a composition for use of the present invention. The composition may additionally comprise antigenic material as described herein and/or chitosan modified by an organic carboxylic acid, or a salt thereof.

In a further preferred embodiment the composition for use of the present invention comprises a mixture of homogenised inactivated dermatophyte microconidia of *Trichophyton mentagrophytes, Microsporum canis, Microsporum canis* var. *obesum, Microsporum canis* var *distortum* and *Microsporum gypseum*. The composition may additionally comprise antigenic material as described herein and/or chitosan modified by an organic carboxylic acid, or a salt thereof.

In a further preferred embodiment the composition for use of the present invention comprises a mixture of homogenised inactivated dermatophyte microconidia of *Trichophyton mentagrophytes, Trichophyton verrucosum, Trichophyton equinum, Trichophyton sarkisovii, Microsporum canis, Microsporum canis* var. *obesum, Microsporum canis* var *distortum* and *Microsporum gypseum*. The composition may additionally comprise antigenic material as described herein and/or chitosan modified by an organic carboxylic acid, or a salt thereof.

In a further preferred embodiment the composition for use of the present invention comprises a mixture of homogenised inactivated dermatophyte microconidia of *Trichophyton mentagrophytes, Trichophyton verrucosum* and *Trichophyton sarkisovii*. The composition may additionally comprise antigenic material as described herein and/or chitosan modified by an organic carboxylic acid, or a salt thereof.

In a further preferred embodiment the composition for use of the present invention comprises homogenised inactivated yeast blastospores of *Candida albicans*, in particular of *Candida albicans* DSM-9456. The composition may additionally comprise antigenic material as described herein and/or chitosan modified by an organic carboxylic acid, or a salt thereof.

In a further preferred embodiment the composition for use of the present invention comprises a mixture of homogenised inactivated dermatophyte microconidia of *Trichophyton mentagrophytes, Trichophyton verrucosum* and *Trichophyton sarkisovii*. The composition may additionally comprise antigenic material as described herein and/or chitosan modified by an organic carboxylic acid, or a salt thereof.

In a further preferred embodiment the composition for use of the present invention comprises antigenic material of yeast blastospores and/or dermatophyte microconidia. Especially preferred is a composition comprising antigenic material of dermatophyte microconidia of *Trichophyton verrucosum*, in particular of the strain *Trichophyton verrucosum* DSM-28406.

In a further preferred embodiment the composition for use of the present invention comprises a mixture of homogenised inactivated dermatophyte microconidia of one, two, three, four, five, six, seven, eight, nine or ten of the above listed dermatophytes and antigenic material of one, two, three, four, five, six, seven, eight, nine or ten of the above listed dermatophytes and/or one, two, three or four of the above listed yeasts.

In a further preferred embodiment the composition for use of the present invention comprises a mixture of antigenic material of dermatophyte microconidia of one, two, three, four, five, six, seven, eight, nine or ten of the above listed dermatophytes with homogenized inactivated yeast blastospores of one, two, three or four *Candida* strains, in particular of *Candida albicans*, more particularly of *Candida albicans* DSM-9456, *Candida albicans* DSM-9457, *Candida albicans* DSM-9458, or *Candida albicans* DSM-9459.

In a further preferred embodiment the composition for use of the present invention comprises a mixture of antigenic material of blastospores of one, two, three or four *Candida* strains, in particular of *Candida albicans*, more particularly of *Candida albicans* DSM-9456, *Candida albicans* DSM-9457, *Candida albicans* DSM-9458, or *Candida albicans* DSM-9459, with homogenised inactivated dermatophyte microconidia of one, two, three, four, five, six, seven, eight, nine or ten of the above listed dermatophytes.

The antigenic material of yeast blastospores and/or dermatophyte microconidia comprises preferably polysaccharides and/or glycopeptides isolated from keratinophilic fungi or yeasts. The antigenic material comprising such polysaccharide and/or glycopeptides can be antigenic nonsoluble material (ANMP), antigenic soluble material (ASMP) or antigenic exogenous material (AEMP). The keratinophilic fungi are preferably of the species *Trichophyton* or *Microsporum*, more preferably *Trichophyton verrucosum*, *Trichophyton mentagrophytes*, *Trichophyton equinum*, *Trichophyton sarkisovii*, *Trichophyton rubrum*, *Trichophyton mentagrophytes*, *Microsporum gypseum* and *Microsporum canis*, and the keratinophilic yeasts are preferably of the species *Candida*, more preferably *Candida albicans*. Especially preferred is antigenic material derived from *Trichophyton mentagrophytes* DSM-7279, *Trichophyton verrucosum* DSM-28406, *Trichophyton rubrum* DSM-9469, *Trichophyton rubrum* DSM-9470, *Trichophyton rubrum* DSM-9471, *Trichophyton rubrum* DSM-9472, *Candida albicans* DSM-9456, *Candida albicans* DSM-9457, *Candida albicans* DSM-9458, and *Candida albicans* DSM-9459. The antigenic material is, for example, obtainable by the method disclosed in WO 97/07232.

In general for obtaining ANMP, the fungal cells belonging to the group of keratinophilic fungi or yeasts are treated under aqueous alkaline conditions, the solid and liquid phases of the preparation are separated, and after separation the solid phase is treated with mineral or organic acid. The treatment under aqueous alkaline conditions is preferably performed with about 0.1 to 5% (w/v) KOH or NaOH at about 20° C. to 150° C. for up to 30 h. The solid phase is preferably treated with 0.2 to 1.5 M organic acid or 0.05 to 1 M mineral acid and washed with an aqueous solution. More specifically, the keratinophilic fungi or yeasts are preferably cultivated on Agar plates. One preferred medium is for example malt extract agar from Oxoid. Other media that will ensure growth of keratinophilic fungi or yeast may be used as well. The resulting fungal biomass is lifted off and treated with the aqueous solution of alkali. Subsequently, the solid and liquid phases of the preparation are separated, for example by centrifugation, filtration or sedimentation. Preferably, the separation is performed by centrifugation, e.g. at 3500 g, which allows good separation of the fungal cell debris. Both the treatment under aqueous alkaline conditions and the separation step may be repeated several times. After alkaline treatment, the resulting supernatant is treated under the acidic aqueous conditions as outlined above. For example, HCl or acetic acid can be used. The treatment with acid is preferably performed for about 0.5 to about 3 hours. The temperature is preferably in the range of about 70 to about 100° C. The aqueous solution for washing is preferably distilled water. Advantageously, the washing is repeated about five times. Finally, the solid phase is lifted off and homogenized in water for injection or in an aqueous solution of 0.1-0.9% solution of chitosan modified by an organic carboxylic acid, or a salt thereof. The homogenization is preferably performed in a volume of about 100 to about 500 ml. The concentration of particles is then preferably adjusted to about 30 to 90 million particles per ml. Finally, the preparation comprising the antigenic material can be lyophilised and stored under dry conditions.

ASMP can generally be obtained as follows: Fungal cells of keratinophilic fungi or yeasts are treated under aqueous alkaline conditions, the solid and liquid phases of the preparation are separated, after separation the supernatant is treated with mineral or organic acid, and after separation ASMP is precipitated from the supernatant. More particularly, keratinophilic fungi or yeasts are cultivated on Agar plates, for example as described in EP 0564620. One preferred medium is for example malt extract agar from Oxoid. Other media that will ensure growth of keratinophilic fungi or yeast may be used as well. The resulting fungal biomass is lifted off and treated with an aqueous solution of alkali. Preferred aqueous alkaline solutions are NaOH or KOH at preferred concentrations of 0.1-5% (w/v). Alkaline treatment is preferably performed at about 20-150° C. for up to 30 h. Following the processing under aqueous alkaline conditions, the solid and liquid phases of the preparation are separated, for example, by centrifugation, filtration or sedimentation. Preferably, the separation is achieved by centrifugation, which ensures good separation of the fungal cell debris, for example, at forces of about 3500 g. The treatment under aqueous alkaline conditions, as well as the separation step, may be repeated several times. After the alkaline treatment and separation, the resulting supernatant is treated under acidic aqueous conditions, e.g. 0.2-1.5M organic acid or 0.05-1M mineral acid. For example, HCl or acetic acid can be used, preferably at pH values of about pH 2.5 to pH 4.5. Preferably, the treatment under aqueous acidic conditions is for about 2 to 4 hours at temperatures of about 4 to 8° C., whereafter separation of the solid and liquid layers takes place. The treatment under aqueous acidic conditions, as well as the separation step, may be repeated several times, preferably under conditions as above indicated. Then, the supernatant from the separation step is subject to a precipitation step. Preferably, the precipitation is performed by adding a suitable organic solvent, e.g. an alcohol such as a lower alkanol, for example methanol or ethanol. A ratio of one volume supernatant to 2-5 volumes of alcohol will result in a good precipitation of the antigenic material. Other nonalcoholic precipitation procedures known to the person skilled in the art may be used as well, for example, ammonium sulphate or other salt precipitation. The solid phase is then subject to a further separation step, preferably under conditions as described above. The resulting solid phase is recovered and, if desired, dissolved in an aqueous solution, preferably in distilled water, typically in a volume of about 25 to 100 ml. Finally, the ASMP preparation can be lyophilised and stored for prolonged time periods under dry conditions.

AEMP can generally be obtained as follows: fungal cells of keratinophilic fungi or yeasts are cultivated in liquid medium, the solid phase and liquid phases of the preparation are separated, and after separation AEMP is precipitated from the supernatant. More particularly, keratinophilic fungi or yeasts may be incubated in aqueous solution or cultivated in liquid medium. The cultivation may be for up to about 240 to 250 hours. The volume of the solution or culture is here defined as primary volume (PV). Distilled water can be used as well as media described in EP 0564620. After incubation or cultivation, the fungal cells are separated, for example, by centrifugation, filtration or sedimentation, preferably by centrifugation under conditions as described above. Optionally, the resulting supernatant is then lyophilised and subsequently dissolved in aqueous solution, preferably in water. Preferably, the volume of water is about 0.1 to 0.2 volumes of the primary volume (PV). The resulting solution or the resulting supernatant obtained after separation is then subject to a precipitation step. Preferably, the precipitation is performed by adding a suitable organic solvent, e.g. an alcohol such as a lower alkanol, for example methanol or ethanol. A ratio of one volume supernatant to about 1 to 5 volumes of alcohol will result in a good precipitation of the antigenic material. Other nonalcoholic precipitation procedures known to the person skilled in the art may be used as well, for example ammonium sulphate or other salt precipitation. The resulting precipitate is recovered and, if desired, dissolved in an aqueous solvent, preferably in distilled water. Preferably, about 0.5 to 50 mg of the precipitate are dissolved in 1 ml aqueous solvent. Finally, the AEMP solution can be lyophilised and stored for prolonged time periods under dry conditions, preferably at about 2 to 10° C.

In a highly preferred embodiment of the present invention the composition for use of the present invention comprises the strain *Trichophyton verrucosum* BINO 348-DSM 28406, antigenic material thereof and/or homogenised inactivated dermatophyte microconidia thereof. The composition may additionally comprise antigenic material as described herein and/or chitosan modified by an organic carboxylic acid, or a salt thereof or a hydro colloid according to the present invention.

In further highly preferred embodiments of the present invention the dermatophyte microconidia of *Trichophyton verrucosum* of the embodiments as outlined above are dermatophyte microconidia of the strain *Trichophyton verrucosum* BINO 348-DSM 28406. However, the embodiments of the present invention as outlined above may also additionally comprise dermatophyte microconidia of the strain *Trichophyton verrucosum* BINO 348-DSM 28406.

In a further highly preferred embodiment the composition for use of the present invention comprises a mixture of homogenised inactivated dermatophyte microconidia of *Trichophyton verrucosum* BINO 348-DSM 28406 and homogenized inactivated yeast blastospores of *Candida albicans*. The composition may additionally comprise antigenic material as described herein and/or chitosan modified by an organic carboxylic acid, or a salt thereof a hydro colloid according to the present invention.

Thus, the present invention also refers to strain *Trichophyton verrucosum* DSM-28406. In a further aspect the present invention relates to homogenised inactivated dermatophyte microconidia of *Trichophyton verrucosum* DSM-28406. Further, the present invention relates to antigenic material, including ANMP, AEMP and ASMP, of dermatophyte microconidia of *Trichophyton verrucosum* DSM-28406.

In addition, the present invention refers to the strain *Trichophyton verrucosum* DSM-28406, homogenised inactivated dermatophyte microconidia of *Trichophyton verrucosum* DSM-28406 and antigenic material, including ANMP, AEMP and ASMP, of dermatophyte microconidia of *Trichophyton verrucosum* DSM-28406 for use in human and/or veterinary medicine. In particular, the present invention refers to the strain *Trichophyton verrucosum* DSM-28406 homogenised inactivated dermatophyte microconidia of *Trichophyton verrucosum* DSM-28406 and antigenic material of dermatophyte microconidia of *Trichophyton verrucosum* DSM-28406 for use in a method of treating and/or preventing of hoof- and claw diseases in animals, lameness, digital dermatitis, interdigital dermatitis, interdigital phlegmone and dermatophytosis in animals and warts in humans. The animals are preferably mammals, more preferably bovidae and/or pigs, most preferably cattle.

In addition, the present invention refers to a composition comprising homogenised inactivated dermatophyte microconidia of the strain *Trichophyton verrucosum* DSM-28406. The present invention also refers to a composition comprising antigenic material of dermatophyte microconidia of the strain *Trichophyton verrucosum* DSM-28406. The compositions of the present invention are preferably pharmaceutical compositions. The present invention also refers to a composition comprising homogenised inactivated dermatophyte microconidia of the strain *Trichophyton verrucosum* DSM-28406 for use in human and/or veterinary medicine, in particular for use in a method of treating and/or preventing hoof- and claw diseases in animals and lameness, digital dermatitis, interdigital dermatitis, interdigital phlegmone, dermatophytosis in animals and warts in humans. The present invention also refers to a composition comprising antigenic material of dermatophyte microconidia of the strain *Trichophyton verrucosum* DSM-28406 for use in human and/or veterinary medicine, in particular for use in a method of treating and/or preventing hoof- and claw diseases in animals and lameness, digital dermatitis, interdigital dermatitis, interdigital phlegmone, dermatophytosis in animals and warts in humans. The animals are preferably mammals, more preferably bovidae and/or pigs, most preferably cattle.

Antigenic material, including ANMP, ASMP and AEMP, of dermatophyte microconidia of the strain *Trichophyton verrucosum* DSM-28406 is obtainable by the same method as outlined above for antigenic material of yeast blastospores and/or dermatophyte microconidia in general.

The composition for use of the present invention and the composition of the present invention are summarized in the following as "compositions of the present invention". Compositions of the present invention comprising dermatophyte microconidia of only one strain or yeast blastospores of only one strain can be prepared as follows:

(a) growing a dermatophyte and a yeast, respectively, on suitable solid medium, harvesting and homogenising the dermatophyte, and
(b) inactivating the homogenate obtained in step (a)

The compositions of the present invention comprising a mixture of dermatophyte microconidia and/or yeast blastospores can be prepared as follows:
(a) growing one dermatophyte strain and two, three, four, five, six, seven, eight, nine or ten distinct strains of dermatophytes, respectively, separately on suitable solid medium, harvesting each culture and homogenising each culture separately, and
(b) optionally, growing one yeast strain and two, three or four distinct strains of yeast, respectively, separately on suitable solid medium, harvesting each culture and homogenising each culture separately, and
(c) combining and inactivating the homogenates obtained in step (a) and optionally obtained in step (b).

The growing of the dermatophytes of the above described preparation processes is preferably done on agar and wort in culture flasks. Preferably, the culture is performed for about 15 to about 30 days. Preferably, the cultivation is performed at a temperature of about 26° C. to about 28° C.

The growing of the yeasts of the above described preparation processes is preferably done on malt extract-agar or agar Sabouraud in culture flasks. Preferably, the culture is performed for about 4 to about 7 days. Preferably, the cultivation is performed at a temperature of about 28 to about 37° C.

After cultivation the dermatophytes and yeasts, respectively, step is homogenized to obtain a fine suspension. Preferably the homogenization is performed in deionized water, in an aqueous solution comprising about 0.1 to 0.3% fermented hydrolyzed muscle protein or about 0.1 to 1% soy or pork peptone in combination with about 5 to 6% glucose and about 0.1 to 1% yeast extract, or in an aqueous solution comprising 0.1-0.9% (w/v) chitosan modified by an organic carboxylic acid, or a salt thereof.

Suitable volumes for homogenization are about 100 to 500 ml. Preferably, the concentration of microconidia and blastospores, respectively, is adjusted to about 30 to about 90 million microconidia and blastospores, respectively, per ml or to about 250 to about 500 thousand, more preferably about 250 to about 400 thousand microconidia and blastospores, respectively, per ml. Then, the suspension may optionally be additional adjusted to about 40, 50 or 60 million of microconidia and blastopores, respectively, per ml or to about 250 to about 500 thousand, more preferably to about 250 to about 400 thousand microconidia and blastospores, respectively, per ml with distilled water, physiological salt solution as e.g. sodium chloride or another suitable solution.

In case of the preparation of a mixture, the single suspensions are preferably adjusted to the same amount of microconidia and blastospore, respectively, per ml and equal volumes of each culture in suspension are mixed in a single container.

The inactivation is preferably performed by using thiomersal, formaldehyde and/or 2-propiolactone. The agents for inactivating can be added directly to the cell suspension. Preferred is an inactivation by adding thiomersal in a ratio of about 1:11000 to about 1:25000 (w/v). Also preferred is an inactivation by adding formaldehyde to reach an end concentration of about 0.2% to about 0.4% (v/v). Subsequently, the mixture is preferably incubated. The incubation can be performed for about 1 to 30 days at a temperature of about 20° C. to about 37° C. Preferred is incubation for about 1 to 3 days at room temperature, for about 5 to 7 days at 37° C., for about 30 days at room temperature or for about 30 days at about 26° C. to 28° C.

In a preferred embodiment the microconidia of the compositions of the present invention are in a swollen condition and/or have germ tubes. More preferably, at least 50% of the blastospores and/or microconidia are in a swollen condition and/or have germ tubes.

The swollen condition and/or the germ tubes of dermatophytes can e.g. be obtained by a second incubation step. Said second incubation step is preferably performed after the homogenization and before inactivation as described above. For performing the second cultivation step the microconidia suspension is placed in a separate vessel containing the same medium of the first incubation step. The second cultivation step is preferably performed for about 10 to about 48 hours. The second cultivation step is preferably performed at a temperature of about 28° C. Preferably, the second cultivation step is continued until at least 50% of the microconidia display a swollen or germinating condition and no more than about 7 to 10% of the cells display a second mycelial branch. The diameter of swollen and germinated microconidia is increased by about 1.2 or more compared to regular microconidia.

The chitosan modified by an organic carboxylic acid, or a salt thereof can also be called chitosan variant or chitosan derivative. It is preferably obtainable by contacting chitosan with an organic carboxylic acid or salt thereof. Said contact is preferably performed by incubating chitosan in an aqueous solution of an organic carboxylic acid or a salt thereof, more preferably by incubating chitosan in an aqueous solution of valeric acid, lactic acid, para-aminobenzoic acid or glucuronic acid or a salt thereof, in particular chloride of valeric acid. Preferably, said incubation is performed by mixing and/or under stirring.

Thus, the chitosan modified by an organic carboxylic acid or a salt thereof is preferably obtainable by a method comprising
(a) incubating chitosan in an aqueous solution of an organic carboxylic acid or a salt thereof.

In a preferred embodiment the chitosan is firstly dissolved under acidic aqueous conditions and subsequently precipitated by increasing the pH value to a pH value of about 8.0 to about 8.5 before it is incubated in the aqueous solution of the organic carboxylic acid or the salt thereof as described above.

Thus, the chitosan modified by an organic carboxylic acid, or a salt thereof is preferably obtainable by a method comprising dissolving chitosan in an aqueous solution of an acid
(ii) increasing the pH value until chitosan is precipitated
(iii) recovering the precipitated chitosan, and
(a) incubating the recovered chitosan of step (iii) in an aqueous solution of an organic carboxylic acid or a salt thereof.

The organic carboxylic acid or a salt thereof of step (a) has preferably a pKs of about 2 to about 5, more preferably of about 2.3 to about 4.9. More preferably said organic carboxylic acid is valeric acid, lactic acid, para-aminobenzoic acid or glucuronic acid or a salt thereof, in particular chloride of valeric acid. Said carboxylic organic acid or a salt thereof is preferably used in a concentration of about 0.2 M to about 22.5 M. The incubation of chitosan and the recovered chitosan of step (iii), respectively, and the aqueous solution of the organic carboxylic acid or a salt thereof as outlined in step (a) results in the solution of the chitosan, the modification of the chitosan and/or the formation of a gel. Preferably, the pH value of the aqueous solution in step (a) is about 5 to about 6 or about 5.0, 5.1, 5.2, 5.3, 5.4, 5.5, 5.6, 5.7, 5.8, 5.9 or 6.0. Preferably, the modification of the chitosan takes place in an aqueous solution comprising about 1 mM to about 100 mM of the organic carboxylic acid or a salt thereof, more preferably about 1 mM to about 10 mM.

Preferably, step (a) is performed until the chitosan is modified and dissolved. It is preferably performed by mixing chitosan with an aqueous solution of the organic carboxylic acid or a salt thereof or by suspending chitosan under aqueous conditions and adding the organic carboxylic acid to the suspension. It is preferably performed under stirring for about 1 to about 72 hours, more preferably for about 24 to about 48 hours. Step (a) may comprise the addition of a further acid or may be performed in the presence of a further acid. Said further acid is preferably a mineral acid, an organic acid or a salt of said mineral acid or organic acid. Preferably, the mineral acid is HCl or $H_2SO_4$ and the organic acid is glutamic acid, para-aminobenzoic acid or lactic acid. The mineral or organic acid is preferably added or present in an amount to adjust the pH value of the mixture of step (a) to a pH value of about 5 to about 6 or about 5.0, 5.1, 5.2, 5.3, 5.4, 5.5, 5.6, 5.7, 5.8, 5.9 or 6.0. The addition of a further acid may support the dissolution and/or the modification of the chitosan e.g. by decreasing the time which is necessary to dissolve the modified chitosan.

The concentration of chitosan in step (a), or if the method comprises a step (i) for step (i), is preferably about 1 g to about 20 g chitosan per liter, more preferably about 5 g to about 15 g chitosan per liter, most preferably about 8 to about 10 g chitosan per liter.

The chitosan used for step (a), or if the method comprises a step (i) for step (i), may be commercially available chitosan or chitosan isolated from any natural source comprising chitosan such as biomass comprising chitosan. Alternatively, chitin may be used which is deacetylated to obtain chitosan prior to step (a), or if the method comprises a step (i) prior to step (i). Said chitin may be commercially available or it may be isolated from a natural source comprising chitin such as biomass comprising chitin. The biomass for chitin and/or chitosan isolation is preferably biomass of fungi, insects and/or crustaceans. The deacetylation of chitin can be performed by known methods in the art as e.g. by using sodium hydroxide (NaOH) in excess as a reagent and water as a solvent or by enzymatic methods. The isolation of chitosan and/or chitin from natural sources can also be performed by known methods in the art.

The chitosan used for step (a), or if the method comprises a step (i) for step (i), has preferably a degree of deacetylation of about 62% to about 95%, more preferably of about 80% to about 94%, more preferably of about 89% to about 93% or of about 93% to about 98%, of about 93% to 95%, of about 95% to about 98%, or of at least 60%, more preferably of at least 70%, 80%, 90% or 95%, or a degree of deacetylation of about 60% to about 100%, more preferably of about 80% to about 95%, even more preferably of about 90% to about 95%, most preferably about 77% to about 80%. The chitosan used for step (a), or if the method comprises a step (i) for step (i), has preferably a molecular weight or an average molecular weight of about 50 Da to about 700 kDa, in particular of about 15 kDa to about 500 kDa, more particular of about 15 kDa to about 150 kDa, or of about 80 kDa to about 200 kDa, of about 150 kDa to about 300 kDa, of about 100 kDa to about 250 kDa or of about 300 kDa to about 700 kDa.

The chitosan used for step (a), or if the method comprises a step (i) for step (i), has preferably a viscosity of about 50 to 400 MPas, more preferably about 70 to about 150 MPas or about 151 to about 350 MPas.

Before the chitosan is used in step (a), or if the method comprises a step (i) in step (i), the chitosan may be sterilized by autoclaving. Said sterilization may result in that the modified chitosan is less toxic, better tolerated by any subject and/or results in less unintended side-effects.

Preferably, step (i) is performed by the use of an aqueous solution of an weak acid, preferably by an organic acid or a salt thereof, more preferably by acetic acid, valeric acid, lactic acid, para-aminobenzoic acid or glucuronic acid or a salt thereof, in particular chloride of valeric acid. The acid is preferably used in a concentration of about 0.8% to about 2%. Step (i) is preferably performed under stirring. The stirring may be performed for about 2 hour to about 24 hours. Preferably, step (i) is performed until a gel or gel suspension is obtained. Unsolved particles may be removed, e.g. by filtration. For example, a metal grid with a cell of 200 µm to 300 µm may be used for such a filtration.

Step (ii) is preferably performed by increasing the pH value of the gel or gel suspension obtained in step (i) until a precipitate is formed. It is preferably performed under stirring. It is preferably performed by treating chitosan under aqueous alkaline conditions, more preferably under aqueous alkaline conditions comprising about 0.1 to about 25.0% alkali. In a preferred embodiment the alkali is NaOH. Preferably, said step is performed at a temperature of about 4° C. to about 55° C. Preferably, the treatment is performed for about 20 min to about 2 hours, more preferably for about 30 min to about 70 min, but it may also take up to about 24 h. Preferably, the pH value is increased by adding the alkali to the gel or gel suspension of step (i). Preferably, the pH value is increased to obtain a pH of about 8.0 to about 8.5. Step (ii) may result in a further deacetylation of the chitosan. It may also result in that the modified chitosan is less toxic, better tolerated by any subject and/or results in less unintended side-effects.

Step (iii) is preferably performed by centrifuging the mixture or suspension obtained in step (ii). The centrifugation is preferably performed at about 4000 to about 6000 revolution/min, more preferably at about 5000 revolution/min. The centrifugation is preferably performed for up to 60 minutes.

The methods by which the modified chitosan is obtainable may comprise additional steps. For example, the product obtained in step (ii), may be homogenized. Preferably, the step of homogenization is performed in a closed sterile homogenizer. Alternatively or in addition, the product obtained in step (a) may be dialyzed. The dialysis is preferably performed in a closed system to remove free ions of salts and low molecular weight compounds. Preferably, the dialysis is performed by cross filtration for about 1 to about 6 hours or by membrane filtration against distillate water for about 24 to about 48 hours.

Alternatively or in addition, the methods by which the modified chitosan is obtainable may comprise a further step of preparing the final product. The preparation of the final product may comprise the dilution of the obtained product. Preferably, the product is diluted by the addition of water, more preferably of sterile water for injection. However, the product may also be diluted in any other suitable aqueous solution. Alternatively or in addition, the preparation of the final product may comprise the addition of one or more further compounds, such as diluents or preservatives. Suitable preservatives are for example chlorocresol, thiomersal and formalin. Finally, the final product may be sterilized. Preferably the sterilization is performed by heating, preferably for about 40 to 50 minutes at a temperature of about 65° C. to about 80° C. Preferably, said sterilization is repeated one, two, three, four or five times.

Preferably, the final product has a concentration of about 0.02 g to about 2 g modified chitosan per liter, more preferably of about 0.04 to about 1 g modified chitosan per liter.

In a preferred embodiment the methods by which the modified chitosan is obtainable comprise the steps as described in the Examples. For example, the methods may comprise the following steps:
optionally sterilizing chitosan e.g. by autoclaving,
(i) dissolving chitosan in an aqueous solution of an acid, in particular in the presence of an acetic acid,
optionally removing undissolved particles e.g. by filtration,
(ii) increasing the pH value until chitosan is precipitated,
(iii) recovering the precipitated chitosan,
optionally homogenizing the recovered chitosan under aqueous conditions,
(a) incubating the recovered chitosan of step (iii) or the homogenized recovered chitosan in an aqueous solution of an organic carboxylic acid or a salt thereof, optionally in the presence of a further mineral acid or organic acid,
optionally dialyzing the product obtained in step (a),
optionally adding further compounds, such as diluents or preservatives, and
optionally sterilizing the final product e.g. by heating.

Preferably, the order of the steps as outlined above corresponds to the order as listed above. However, as known by the person skilled in the art the order of single steps may be varied as long as the same effects are achieved. For example, diluents such as water may be added in various stages of the method as described above.

In a preferred embodiment of the present application the modified chitosan, chitosan derivative or chitosan variant is a Polyamino-sugar colloid, preferably a hydro colloid. In another preferred embodiment of the present application the hydro colloid is a Chitosan-Glucuronic acid-Hydro-Colloid or Chitosan-p-Aminobenzoic acid-Hydro-Colloid or Chitosan-Valeric acid-Hydro-Colloid. In another preferred embodiment of the present application the Chitosan-Glucuronic acid-Hydro-Colloid has the chemical formula: $(C_6H_{11}O_4N)_x$ $(C_8H_{13}O_5N)_y$ $(C_6H_{10}O_7)_z$ $(H_2O)_m$. Preferably, the Chitosan-Glucuronic acid-Hydro-Colloid has the following molecular weight: $x*(161)+y*(203)+z*(194.14)+m*(18)$. In another preferred embodiment of the present application the Chitosan-p-Aminobenzoic acid-Hydro-Colloid has the chemical formula: $(C_6H_{11}O_4N)_x$ $(C_8H_{13}O_5N)_y$ $(C_7H_7O_2N)_z$ $(H_2O)_m$. Preferably, the Chitosan-p-Aminobenzoic acid-Hydro-Colloid has the following molecular weight: $x*(161)+y*(203)+z*(137.14)+m*(18)$. In another preferred embodiment of the present application the Chitosan-Valeric acid-Hydro-Colloid has the chemical formula: $(C_6H_{11}O_4N)_x$ $(C_8H_{13}O_5N)_y$ $(C_6H_{10}O_2)_z$ $(HCl)_z$ $(H_2O)_m$. Preferably, Chitosan-Valeric acid-Hydro-Colloid has the following molecular weight: $x*(161)+y*(203)+z*(102)+z*(36.5)+m*(18)$.

In another preferred embodiment of the present application the modified chitosan, chitosan derivative or chitosan variant is a natural white to yellowish viscous liquid. Preferably, the modified chitosan, chitosan derivative or chitosan variant has typical odor of the carboxylic acid, preferably the typical odor of valeric acid.

In another preferred embodiment, the modified chitosan, chitosan derivative or chitosan variant contains about 0.2% pentanoly chloride, or 0.2% Glucuronic acid, or 0.2% p-Aminobenzoic acid.

In another preferred embodiment, the modified chitosan, chitosan derivative or chitosan variant contains about 1.0% pentanoly chloride.

In another preferred embodiment, the modified chitosan, chitosan derivative or chitosan variant contains 1% chitosan residue from drying chitosans.

In another preferred embodiment, the modified chitosan, chitosan derivative or chitosan variant has about 10 to about 1000 mOsmol, preferably about 10 to about 200 mOsmol, most preferably about 100 mOsmol.

In another preferred embodiment, the modified chitosan, chitosan derivative or chitosan variant is a hydro colloid comprising:
(i) 0.1% to 5% (w/v) chitosan and 0.001 to 5% (w/v) valeric acid, or a salt thereof, preferably chloride of valeric acid or
(ii) 0.1% to 5% (w/w) chitosan and 0.001 to 5% (w/w) glucuronic acid or p-aminobenzoic acid or a salt thereof.

In another preferred embodiment, the modified chitosan, chitosan derivative or chitosan variant is a hydro colloid comprising:
(i) 0.1% to 3% (w/v) chitosan and 0.001 to 2% (w/v) valeric acid or a salt thereof, preferably chloride of valeric acid, or
(ii) 0.1% to 3% (w/w) chitosan and 0.001 to 2% (w/w) glucuronic acid or p-aminobenzoic acid or a salt thereof.

In another preferred embodiment, the modified chitosan, chitosan derivative or chitosan variant is a hydro colloid comprising:
(i) 0.1% to 1.2% (w/v) chitosan and 0.001 to 1% (w/v) valeric acid or a salt thereof, preferably chloride of valeric acid, or
(ii) 0.1 to 1.2% (w/w) chitosan and 0.001 to 1% (w/w) glucuronic acid or p-aminobenzoic acid or a salt thereof.

In another preferred embodiment, the modified chitosan, chitosan derivative or chitosan variant is a hydro colloid comprising:
(i) 0.1% to 1.2% (w/v) chitosan and
(ii) 0.01 to 0.44% (w/v) valeric acid, or a salt thereof, preferably chloride of valeric acid.

In another preferred embodiment, the modified chitosan, chitosan derivative or chitosan variant is a hydro colloid comprising:
(i) 0.1% to 1.2% (w/w) chitosan and
(ii) 0.001 to 0.6% (w/w) glucuronic acid or a salt thereof.

In another preferred embodiment, the modified chitosan, chitosan derivative or chitosan variant is a hydro colloid comprising:
(i) 0.1% to 1.2% chitosan and
(ii) 0.006 to 1% (w/w) p-aminobenzoic acid or a salt thereof.

Preferably the chitosan of the hydro colloid is a compound of formula [X]n, in which n represents an integer of about 1 to about 5000, in particular an integer of about 300 to about 4000, and X has the following formula (1):

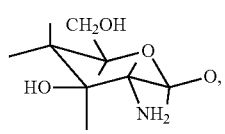

(1)

wherein about 2% to about 38%, more preferably about 5% to about 20% of the X residues constituting said compound are modified by acetylation and wherein all or part of the X residues constituting said compound are modified by an organic carboxylic acid or a salt thereof, In a preferred embodiment, the remaining percentage of the hydro colloid according to the present invention is provided by the dispersion media, preferably water or water and hydrogenchloride (HCl).

In a preferred embodiment, the hydro colloid according to the present invention is used as a dilution, preferably in a dilution of 0 to 10 times.

In an exemplified embodiment the modified chitosan is obtainable by the following procedure:

Chitosan with deacetylation of e.g. 67%, a viscosity of 50-200 mPas can be used as raw material. 40 grams of chitosan is sterilized by autoclaving and 3.5 liters of water for injection are added under stirring. 40 ml of acetic acid are added to the obtained suspension. The final volume is adjusted to a volume of 4 liters with water for injection. The mixture is stirred in a sterile container for about 24 hours until a gel suspension is obtained. Unsolved particles are removed by filtration through a metal grid with a cell size of 200 μm-300 μm. 4 N sodium hydroxide (NaOH) in added dropwise to the prepared mixture to obtain a final pH of 8.0. Upon that white flakes precipitate which contain the chitosan. The suspension is stirred for about 30 minutes. Under constant stirring, 4 mL valerian acid chloride is added dropwise to the suspension. The obtained suspended material is stirred for one hour. Flakes and unsolved particles are separated and subsequently resuspended in 4 liters of sterile water for injections. Under stirring 4N hydrochloric acid is added to obtain a pH of 5.0. The resultant gel is dialysed in a closed system to remove free ions of salts and low molecular weight compounds. After dialysis, the final product is prepared. For obtaining the final product 3 liters of the modified chitosan gel are adjusted to a volume of 25 liters by adding sterile water for injection under stirring. Then, 500 ml of chlorocresol solution containing 30 grams of chlorosresol are added to the mixture. The resultant suspension is adjusted to a volume of 30 liters. The resultant sterile product is dispensed into vials under sterile conditions.

If no specific temperature ranges are given for the method steps as described herein, the steps are preferably performed at room temperature and/or in a range of about 10° C. to about 40° C., more preferably in a range of about 20° C. to about 30° C.

In a preferred embodiment the compositions of the present invention have a concentration of about 40 to about 90 million blastospores per ml, highly preferred is a concentration of about 40 million to 60 million spores per ml. These concentrations are especially preferred if the compositions are for intramuscular administration. In a further preferred embodiment the compositions of the present invention have a concentration of about 0.2 to about 0.4 million spores per ml, highly preferred is a concentration of about 0.25 million to about 0.3 million spores per ml. These concentrations are especially preferred if the compositions are for intracutaneous intramuscular administration.

In a further preferred embodiment the compositions of the present invention have a concentration of about 40 to about 60 million particles of antigenic material of dermatophyte microconidia and/or yeast blastospores per ml.

In a further preferred embodiment the concentration of the chitosan modified by an organic carboxylic acid, or a salt thereof is preferably in the range of about 0.1% to about 0.9% (w/v), more preferably in the range of about 0.1 to about 0.3% (w/v), more preferably in the range of about 0.1 to about 0.3% (w/v).

Surprisingly, it was found that if the composition of the present invention additionally comprise chitosan modified by an organic carboxylic acid, or a salt thereof the homogenised inactivated dermatophyte microconidia and/or inactivated homogenized yeast blastospores can be used in a about 50 times less dose.

The compositions of the present invention may additionally comprise pharmaceutically acceptable carrier, excipients and/or supports.

The compositions of the present invention are able to modulate the immune system, i.e. they have immunostimulatory properties. They can be used as a vaccine for preventing the subject from the diseases as outlined above. Alternatively or in addition, they can be used to treat and cure the subject from the diseases as outlined above. The compositions can be administered by known administration routes as e.g. parenterally, by intramuscular injection, by intracutaneous injection, by percutaneous injection and/or topically, preferably cutaneously. They may be administered in the absence or in the presence of one or more additional immunostimulatory substances. In one embodiment said one or more additional immunostimulatory substances are administered separately to the compositions of the present invention. In another embodiment the one or more additional immunostimulatory substances are comprised in or added to the compositions of the present invention.

Said one or more immunostimulatory substance is preferably an adjuvant, preferably selected from the group consisting of vitamin-E acetate, o/w-emulsion, aluminum phosphate, aluminum oxide, aluminum hydroxide/methyl cellulose gel, an oil-emulsion, muramil-dipeptides, Freund's adjuvants and saponins and/or at least one cytokine, preferably selected from the group consisting of IL 2, IL 12 and INF-Gamma.

In a more preferred embodiment the compositions of the present invention additionally comprise chitosan modified by an organic carboxylic acid, or a salt thereof or a hydro colloid according to the present invention.

In a preferred embodiment the compositions of the present invention is a vaccine and/or is used as a vaccine.

The present invention relates also to a pharmaceutical composition comprising antigenic material of keratinophilic fungi or keratinophilic yeasts as described above. Such pharmaceutical composition may additionally comprise a pharmaceutical acceptable diluent, excipient or carrier.

In a further aspect the present invention relates to a composition comprising antigenic material of keratinophilic fungi or keratinophilic yeasts as described above for use in a method of treatment of the animal body by therapy. Such method typically comprises administering to a subject an effective amount of antigenic material of keratinophilic fungi or keratinophilic yeasts as described above or a composition or a pharmaceutical composition as described above. The subject may for example an animal, in particular a mammal, more preferably bovidae and/or pigs, most preferably cattle. In particular, the antigenic material of keratinophilic fungi or keratinophilic yeasts as described above or a composition or a pharmaceutical composition as described above may be used in methods for the treatment or prevention of hoof- and claw diseases as described above. The method of treatment may comprise the treatment and/or prevention of bacterial, mycotic and/or viral infections of the skin, the leg, the hoof, the claws, the back of the foot and/or the interdigital space. Said infections may be caused by

*Dichelobacter nodosus, Fusobacterium necroforun, Fusobacterium* spp, *Treponema* spp such as *T. phagedenis, T. vincentii*, and *T. denticola, Campylobacter* spp, *Staphylococcus aureus, Escherichia coli, Arcanobacterium pyogenes*, and *Prevotella* spp. and/or a virus.

The dosage and route of administration used in a method of treatment (and/or prophylaxis) according to the present invention depends on the specific disease/site of infection to be treated. The route of administration may be for example parenterally, by intramuscular injection, by intracutaneous injection, by percutaneous injection, topically, cutaneously or any other route of administration.

For example, the dosage and route of administration used in a method of treating and/or preventing hoof- and claw diseases, in particular ID, DD and/or IP, in cattle may be as follows:

| route of administration | concentration [million blastspores/ microconidia/ml] | frequency of drug administration | number of sites | interval between drug administration [days] | dose [ml] |
| --- | --- | --- | --- | --- | --- |
| intramuscular | 10-150, more preferably 30-90, more preferably 40-60, or 20, 30, 40, 50, 60, 70, 80, 90, or 100 | 1, 2, 3, 4 or 5 | 1 or 2 | 5-21 days, more preferably 7-10 days or 5, 6, 7, 8, 9, 10, 11, 12, 13 or 14 days | 0.5-10, more preferably 1-5, or 0.5, 1, 2, 2.5, 3, 4, 5, or 6 |
| intracutanous | 0.1-0.6, more preferably 0.25-0.4, or 0.1, 0.2, 0.25, 0.3, 0.4, 0.5, or 0.6 | 1, 2, 3, 4 or 5 | 1, 2 or 3 | 5-21 days, more preferably 7-10 days, or 5, 6, 7, 8, 9, 10, 11, 12, 13, 14, 15, 16, 17, 18, 19, 20 or 21 days | 0.2-0.6, more preferably 0.3-0.5, or 0.2, 0.3, 0.4. 0.5, or 0.6 |

The following examples explain the present invention but are not considered to be limiting.

EXAMPLE 1

Vaccine Polivac-TM (manufacturer: "Vetbiochim" LLC, Moscow; Distributor: "Prostore" LLC, Moscow) against dermatophytosis of animals was used for the prophylaxis and treatment of digital and/or interdigital dermatitis and/or interdigital phlegmon in cattle as described below.

EXAMPLE 2

Vaccine Polivac-T (manufacturer: "Vetbiochim" LLC, Moscow; Distributor: "Prostore" LLC, Moscow) against dermatophytosis of cattle was used for the prophylaxis and treatment of interdigital and/or digital dermatitis and/or interdigital phlegmon in cattle as described below.

EXAMPLE 3

Dermatophyte culture of the species *Trichophyton mentagrophytes* DSM-7279 is cultivated on agar/wort, for example in 4 Roux flasks. Each culture is cultivated for 18 days at 28° C.

The fungal masses are lifted off and homogenised in 500 ml deionized water. Then suspension of microconidia is adjusted to 60 million of microconidia per ml with physiological sodium chloride salt solution. The homogenate is inactivated by adding formaldehyde to 0.4% (v/v) in end directly to the cell suspension. The mixture is incubated for 5-7 days at 37° C. The resulting composition is bottled, checked for sterility, safety and amount of microconidia in accordance with usual known methods and can be stored refrigerated at 4-10° C. Vaccine obtainable according to this method was used for the prophylaxis and treatment of interdigital digital dermatitis and/or interdigital phlegmon in cattle as described below.

EXAMPLE 4

Dermatophyte culture of the species *Trichophyton verrucosum* DSM-28406 is cultivated on agar/wort, for example in 10 Roux flasks. Each culture is cultivated for 25 days at 26° C.

The fungal masses are lifted off and homogenised in 300 ml deionized water. The concentration of microconidia is adjusted to 80 million per ml for each homogenate. Then suspension of microconidia is adjusted to 40 million of microconidia per ml with distilled water. The homogenate is inactivated by adding formaldehyde to reach 0.5% (v/v) directly to the cell suspension. The mixture is incubated for 5 days at 37° C. The resulting composition is bottled, checked for sterility, safety and amount of microconidia in accordance with usual methods and stored at 4-8° C. Vaccine obtainable according to this method was used for the prophylaxis and treatment of interdigital, digital dermatitis and interdigital phlegmon in cattle as described below.

EXAMPLE 5

Dermatophyte culture of the species *Trichophyton verrucosum* DSM-28406 is cultivated on agar/wort, for example in 8 Roux flasks. Each culture is cultivated for 30 days at 27° C.

The fungal masses are lifted off and homogenised in 400 ml deionized water. The concentration of microconidia is adjusted to 70 million per ml for each homogenate. Then suspension of microconidia is adjusted to 60 million of microconidia per ml with distilled water. The homogenate is inactivated by adding formaldehyde to reach 0.3% (v/v) directly to the cell suspension. The mixture is incubated for 7 days at 37° C. The resulting composition is bottled, checked for sterility, safety and amount of microconidia in accordance with usual methods and stored at 4-8° C. Vaccine obtainable according to this method was used for the prophylaxis and treatment of interdigital, digital dermatitis and interdigital phlegmon in cattle as described below.

EXAMPLE 6

Dermatophyte culture of the species *Trichophyton verrucosum* DSM-28406 is cultivated on agar/wort, for example in 9 Roux flasks. Each culture is cultivated for 25 days at 28° C.

The fungal mass of the dermatophyte are lifted off and homogenised in 500 ml an aqueous solution of 0.3% fermented hydrolyzed muscle protein in combination with 5% glucose and 0.1% yeast extract. The concentration of microconidia is adjusted to 40 million per ml for homogenate. Then the suspension of microconidia is fermented for 1 day at 28° C., until 65% of the microconidia have germ tubes. After fermentation the cell suspensions is washed with physiological solution of sodium chloride. The homogenate is inactivated by adding thiomersal in a ratio of 1:25000 (w/v) directly to the cell suspension. The mixture is incubated for 30 days at room temperature. The resulting composition is bottled, checked for sterility, safety and immunogenic properties in accordance with accepted methods and can be stored refrigerated at 4-10° C. Composition obtainable according to this method was used for the prophylaxis and treatment of interdigital, digital dermatitis, interdigital phlegmon and dermatophytosis in cattle as described below.

EXAMPLE 7

A variation of the vaccine Polivac-TM against dermatophytosis of animals comprising in comparision to the classical Polivac-TM no *Trichophyton equinum* and *Microsporum* strains (manufacturer: "Vetbiochim" LLC, Moscow; Distributor: "Prostore" LLC, Moscow) was used for the prophylaxis and treatment of interdigital and/or digital dermatitis and/or interdigital phlegmon in cattle as described below.

EXAMPLE 8

Vaccine Polivac-TM against dermatophytosis of animals (manufacturer: "Vetbiochim" LLC, Moscow; Distributor: "Prostore" LLC, Moscow) was used for the prophylaxis and treatment of interdigital and/or digital dermatitis and/or interdigital phlegmon in cattle as described below.

EXAMPLE 9

Vaccine Polivac-TM against dermatophytosis of animals (manufacturer: "Vetbiochim" LLC, Moscow; Distributor: "Prostore" LLC, Moscow) was used for the prophylaxis and treatment of digital and/or interdigital dermatitis and/or interdigital phlegmon in cattle as described below.

EXAMPLE 10

Vaccine Polivac-T against dermatophytosis of cattle (manufacturer: "Vetbiochim" LLC, Moscow; Distributor: "Prostore" LLC, Moscow) was used for the prophylaxis and treatment of interdigital and/or digital dermatitis and/or interdigital phlegmon in cattle as described below.

EXAMPLE 11

Dermatophyte culture of the species *Trichophyton verrucosum* DSM-28406 is cultivated on agar/wort, for example in 10 Roux flasks. The culture is cultivated for 28 days at 28° C.

The fungal mass is lifted off and homogenised in 500 ml deionized water. The concentration of microconidia is adjusted to 50 million per ml in homogenate. Then suspension of microconidia is adjusted to 50 million of microconidia per ml with distilled water.

The species *Candida albicans* DSM-9456 is cultivated on malt extract-agar or agar Sabouraud, for example in 3 Roux flasks. Culture is cultivated for 4 days at 30° C. The blastospores are washed off with a physiological solution of sodium chloride. The concentration of blastospores in suspension is adjusted to 60 million per ml. Equal volumes of each culture in suspension are mixed in a single container. The homogenates are inactivated by adding formaldehyde to reach 0.4% (v/v) in cell suspension. The mixture is incubated for 6 days at 37° C. Composition obtainable according to this method was used for the prophylaxis and treatment of interdigital and/or digital dermatitis and/or interdigital phlegmon in cattle as described below.

EXAMPLE 12

The species *Candida albicans* DSM-9456 is cultivated on agar Sabouraud, for example in 7 Roux flasks. Culture is cultivated for 7 days at 37° C. The blastospores are washed off with sterill water. The concentration of blastospores in suspension is adjusted to 40 million per ml. The homogenate is inactivated by adding formaldehyde to reach 0.5% (v/v) in cell suspension. The mixture is incubated for 7 days at 37° C. Composition obtainable according to this method was used for the prophylaxis and treatment of interdigital and/or digital dermatitis and/or interdigital phlegmon in cattle as described below.

EXAMPLE 13

A solution of chitosan modified by valeric acid chloride was added to the vaccine Polivac-T against dermatophytosis of cattle (manufacturer: "Vetbiochim" LLC, Moscow; Distributor: "Prostore" LLC, Moscow) to reach a final concentration of 0.1% (w/v). The concentration of microconidia was 40 million per ml. Composition obtainable according to this method was used for the prophylaxis and treatment of interdigital and/or digital dermatitis and/or interdigital phlegmon in cattle as described below.

EXAMPLE 14

Dermatophyte culture of the species *Trichophyton verrucosum* DSM-28406 is cultivated on agar/wort, for example in 7 Roux flasks. The culture is cultivated for 27 days at 26° C.

The fungal masses of the dermatophyte is lifted off and homogenised in 500 ml an aqueous solution of 0.2% of chitosan modified by paraaminobenzoic acid. The concentration of microconidia is adjusted to 50 million per ml for each homogenate. The homogenate is inactivated by adding formaldehyde to reach an end concentration of 0.5% (v/v)

directly to the cell suspension. The mixture is incubated for 7 days at 37° C. The composition obtainable according to this method was used for the prophylaxis and treatment of interdigital and/or digital dermatitis and/or interdigital phlegmon and/or dermatophytosis in cattle as described below.

EXAMPLE 15

The species *Candida albicans* DSM-9456 is cultivated on malt extract-agar for 6 Roux flasks. Culture is cultivated for 7 days at 35° C. The blastospores are washed off with a physiological solution of sodium chloride.

The fungal masses is lifted off and homogenised in an 500 ml aqueous solution of 0.1% solution of chitosan modified by valeric acid chloride. The concentration of microconidia is adjusted to 80 million per ml in homogenate. The homogenate is inactivated by adding formaldehyde to reach 0.2% (v/v) in end directly to the cell suspension. The mixture is incubated for 7 days at 37° C. Composition obtainable according to this method was used for the prophylaxis and treatment of interdigital and/or digital dermatitis and/or interdigital phlegmon in cattle as described below.

EXAMPLE 16

The fraction obtainable according to this process consists of antigenic nonsoluble material comprising polysaccharide and/or glycopeptides (ANMD) as disclosed in WO 97/07232. Dermatophyte culture of the species *Trichophyton verrucosum* DSM-28406 is cultivated on agar/wort, for example in 10 Roux flasks. The culture is cultivated for 28 days at 28° C.

The resulting fungal biomass is lifted off and treated with an aqueous solution of alkali. Preferred aqueous alkaline solutions are NaOH at concentration of 3% (w/v). Alkaline treatment is preferably performed at 80° C. for up to 6 h. Following the processing under aqueous alkaline conditions, the solid and liquid phases of the preparation are separated by centrifugation at forces of about 3500 g. After alkaline treatment, the solid phase is treated with 0.2 M acetic acid are added to the solid phase for 1 hour at temperatures of 70° C. After acidic treatment the solid phase is washed with distilled water. The washing is repeated three times. Finally, the solid phase is lifted off and homogenised in 500 ml water for injection. The concentration of the particles is adjusted to 60 million per ml end product. Composition obtainable according to this method was used for the prophylaxis and treatment of interdigital and/or digital dermatitis and/or interdigital phlegmon in cattle as described below.

EXAMPLE 17

The fraction obtainable according to this process consists of antigenic nonsoluble material comprising polysaccharide and/or glycopeptides (ANMP) as disclosed in WO 97/07232. Dermatophyte culture of the species *Trichophyton verrucosum* DSM-28406 is cultivated on agar/wort in 9 Roux flasks. The culture is cultivated for 25 days at 27° C. The resulting fungal biomass is lifted off and treated with an aqueous solution of alkali. Preferred aqueous alkaline solutions are KOH at preferred concentrations of 2% (w/v). Alkaline treatment is preferably at 60° C. for up to 10 h. Following the processing under aqueous alkaline conditions, the solid and liquid phases of the preparation are separated by centrifugation at forces of about 3500 g. The treatment under aqueous alkaline conditions was repeated two times, as well as the separation step by centrifugation at forces of about 3500 g. After alkaline treatment, the solid phase is treated with 0.5M HCl is added to the solid phase for 1.5 hours at temperatures of 80° C. After acidic treatment the solid phase is washed with distilled water two times. Finally, the solid phase is lifted off and homogenised in 500 ml an aqueous solution comprising 0.3% chitosan modified by valeric acid chloride. The concentration of particles is adjusted to 60 million per ml for each homogenate. The composition obtainable according to this method was used for the prophylaxis and treatment of interdigital and/or digital dermatitis and/or interdigital phlegmon in cattle as described below.

EXAMPLE 18

The product is prepared from Chitosan. The product is prepared in two stages. In the first stage a concentrated modified chitosan gel is obtained, in the second stage the final product, which can be used for administration.
The First Step.

Chitosan with deacetylation of 80%, a viscosity of 2751-3250 mPas is used as raw material. 40 grams of the polysaccharide is sterilized by autoclaving and 3.5 liter of water for injection is added under stirring. In the obtained suspension 40 ml of acetic acid are added. The final volume is adjusted with water for injection to 4 liter. Suspended polysaccharide is stirred in a sterile container for 24 hours until a gel suspension is obtained. Unsolved particles are removed by filtration through a metal grid with a pore size of 200 μm-300 μm. 4 N sodium hydroxide (NaOH) is added dropwise to the obtained suspension until the suspension has a pH of 8.0. Upon that white flakes precipitate comprising the chitosan. The suspension is stirred for 30 minutes. 8 mL lactic acid is added dropwise to the suspension under constant stirring. The obtained suspended material is stirred for another hour. Flakes and unsolved particles are separated from the suspension and resuspended in 4 liter water for injection. 4N hydrochloric acid is added under stirring until a pH of 5.6 is reached. The resultant suspension is dialysed in a closed system to remove free ions of salts and low molecular weight compounds. The resultant suspension is a concentrated modified chitosan gel. The modified chitosan concentration is about 0.8% to about 1%. After the dialysis, the polysaccharide is used to prepare the final product.
The Second Step.

For obtaining the final product comprising the modified chitosan obtained in the first step the resultant suspension of the first step is adjusted to a volume of 25 liter by adding sterile water for injection under stirring. Then, 500 ml of chlorocresol solution containing 30 grams chlorocresol are added to the mixture as preservative. The resultant suspension is adjusted to a volume of 30 liter. The resultant sterile product is dispensed into vials under aseptic conditions. Composition obtainable according to this method was used for the prophylaxis and treatment of interdigital and/or digital dermatitis and/or interdigital phlegmon in cattle as described below.

EXAMPLE 19

Dermatophyte culture of the species *Trichophyton verrucosum* DSM-28406 is cultivated on agar/wort, for example in 8 Roux flasks. The culture is cultivated for 30 days at 28° C.

The fungal masses of the dermatophyte is lifted off and homogenised in 500 ml an aqueous solution of 0.1% chitosan modified by valeric acid chloride. The concentration of microconidia is adjusted to 400 thousand per ml for each homogenate. The homogenates are inactivated by adding formaldehyde to reach 0.4% (v/v) in end directly to the cell suspension. The mixture is incubated for 7 days at 37° C. Composition obtainable according to this method was used for the prophylaxis and treatment of interdigital and/or digital dermatitis and/or interdigital phlegmon and/or dermatophytosis in cattle as described below.

EXAMPLE 20

Dermatophyte culture of the species *Trichophyton mentagrophytes* DSM-7279 is cultivated on agar/wort in 6 Roux flasks. The culture is cultivated for 20 days at 26° C.

The fungal masses of the dermatophyte is lifted off and homogenised in 400 ml an aqueous solution of 0.2% chitosan modified by paraaminobenzoic acid. The concentration of microconidia is adjusted to 250 thousand per ml for each homogenate. The homogenates are inactivated by adding formaldehyde to reach 0.3% (v/v) in end directly to the cell suspension. The mixture is incubated for 6 days at 37° C. Composition obtainable according to this method was used for the prophylaxis and treatment of interdigital and/or digital dermatitis and/or interdigital phlegmon and/or dermatophytosis in cattle as described below.

EXAMPLE 21

Cows with clinical evidence of lameness and lesions of the interdigital space, which are typical for DD, ID and IP, were treated with various compositions. The composition was administered by intramuscular injection two times with an interval of 10 days. The dose for composition was 5 ml for each application.

The results are shown in Table 2.

| | | | | Amount of healthy animals | |
|---|---|---|---|---|---|
| No of group | Composition as prepared in example | No of animals | Frequency of drug administration | In 30-35 days after the first application | In 53-55 days after the first application |
| 1 | 1 | 10 | 2 | 4 | 5 |
| 2 | 2 | 10 | 2 | 4 | 5 |
| 3 | 3 | 10 | 2 | 5 | 5 |
| 4 | 4 | 10 | 2 | 4 | 5 |
| 5 | 5 | 15 | 2 | 7 | 7 |
| 6 | 6 | 13 | 2 | 6 | 6 |
| 7 | 7 | 10 | 2 | 4 | 5 |
| 8 | 8 | 11 | 2 | 5 | 6 |
| 9 | 9 | 12 | 2 | 5 | 6 |
| 10 | 10 | 13 | 2 | 6 | 6 |
| 11 | 11 | 14 | 2 | 7 | 7 |
| 12 | 12 | 13 | 2 | 6 | 7 |
| 13 | 13 | 10 | 2 | 5 | 7 |
| 14 | 14 | 12 | 2 | 5 | 7 |
| 15 | 15 | 14 | 2 | 6 | 8 |
| 16 | 16 | 10 | 2 | 5 | 5 |
| 17 | 17 | 12 | 2 | 6 | 6 |
| 18 | 18 | 14 | 2 | 7 | 9 |

No common or local reactions after application of the compositions were observed. Therapeutic efficacies of treatment with different compositions produced as described in Examples 1 to 18 were 40% to 64%.

EXAMPLE 22

Cows with clinical evidence of lameness and lesions of the interdigital space, which are typical for DD, ID and IP, were treated with various compositions. The composition was administered by intracutaneous injection two times with an interval of 7-10 days. The composition dose was 0.4 ml in total which was injected into two sites of the animal.

The results are shown in Table 3.

| | | | | Amount of healthy animals | |
|---|---|---|---|---|---|
| No of group | Composition as prepared in example | No of animals | Frequency of drug administration | In 30-35 days after the first application | In 53-55 days after the first application |
| 1 | 19 | 100 | 2 | 60 | 85 |
| 2 | 20 | 100 | 2 | 58 | 87 |

No common or local reactions after application of the compositions were observed. Therapeutic efficacy of treatment with different compositions produced according to examples 19 and 20 were about 85% to 87%.

EXAMPLE 23

Cows with clinical evidence of lameness and lesions of the interdigital space, which are typical for DD, ID and IP, were treated with various drugs. The composition prepared in accordance with Example 15 was administered as follows: 2 times intramuscular in a dose of 5 ml at one site with an interval of 10 days.
Clinical Manifestation of Disease:
+ Recovering, or gray, no pain
++ in healing, <2 cm, yellow, light pain
+++ Recovering, or >2 cm, yellow, moderate pain
++++ acute disease>2 cm, red, significant pain
The results are shown in Table 4.

| Before treatment | 30 days after treatment | 58 days after treatment |
|---|---|---|
| 12 animals ++ | 4 animals-healthy<br>4 animals +<br>6 animals ++ | 11 animals-healthy<br>3 animals + |
| 4 animals +++ | 2 animals +++ | 3 animals ++ |
| 4 animals ++++ | 2 animals ++++<br>in total 2 animals were culled for slaughter | in total 3 animals were culled for slaughter |

No common or local reactions after application were observed. Efficacy of treatment was about 70%.

EXAMPLE 24: DOSE TITRATION STUDY

Cows with clinical evidence of lameness, lesions of the interdigital space, which are typical for DD, ID and IP, were treated with various drugs. Therapeutic application of the composition prepared in accordance with Example 14: 3 times intramuscular at one site with an interval of 7 days.
Clinical Manifestation of Disease:
+ Recovering, or gray, no pain
++ In healing, <2 cm, yellow, light pain
+++ Recovering, or >2 cm, yellow, moderate pain
++++ acute disease>2 cm, red, significant pain
The results are shown in Table 5.

| Before treatment | 51 days after treatment Dose - 5 ml | Before treatment | 51 days after treatment Dose - 3 ml |
|---|---|---|---|
| 19 animals +++ | 5 animals-healthy<br>7 animals +<br>5 animals ++<br><br>2 animals were culled for slaughter | 18 animals +++ | 1 animal-healthy<br>4 animals +<br>6 animals ++<br>2 animals +++<br>5 animals were culled for slaughter |

No common or local reactions after application were observed. Efficacy of treatment with dose 5 ml was about 63% and 3 ml-28%.

EXAMPLE 25

Cows with clinical evidence of lameness and lesions of the interdigital space, which are typical for DD, ID and IP, were treated. Therapeutic application of the composition prepared in accordance with Example 14: intramuscular, 2 times at one site in dose of 5 ml with an interval of 10 days.
Summary of Investigation:

| Before treatment | |
|---|---|
| Amount of animals/amount of limbs with lameness | 100/138 |
| 52 to 54 days after last treatment | |
| Amount of animals/amount of limbs with lameness | 29/29 |
| Amount of healthy animals | 71 |
| Degrease of limbs with lameness | 78.99% |

EXAMPLE 26—DOSE TITRATION STUDY

Treatment of cows against DD, ID and IP was done. Prophylactic application of a composition prepared in accordance with Example 14: intramuscular, 2 times with an interval of 10 days.
Clinical Manifestation of Disease was Investigated:
+ Recovering, or gray, no pain
++ in healing, <2 cm, yellow, light pain
+++ Recovering, or >2 cm, yellow, moderate pain
++++ acute disease>2 cm, red, significant pain
The results are shown in Table 6.

| 73 days after application | | |
|---|---|---|
| Dose 1 ml | Dose 2.5 ml | Control |
| 100 animals | 100 animals | 215 animals |
| 7 animals + | 7 animals + | 21 animals +<br>18 animals ++<br>6 animals +++ |

No common and local reactions after application of the composition were observed. Efficacy of treatment with doses of 1 ml and 2.5 ml was about 93%. 45 animals (about 21%) from control group were with clinical symptoms of DD, ID and IP.
The results are shown in Table 7.

| 107 days after application of composition | | |
|---|---|---|
| Dose 1 ml | Dose 2.5 ml | Control |
| 100 animals | 100 animals | 215 animals |
| 7 animals + | 9 animals + | 11 animals +<br>12 animals ++ |
| 4 animals-culling for slaughter | 4 animals-culling for slaughter | 9 animals +++<br>27 animals-culling for slaughter |

Efficacy of treatment with doses of 1 ml and 2.5 ml was about 87%-89%. 59 animals (about 27%) from control group were with clinical symptoms of DD, ID and IP.
The results are shown in Table 8.

| 170 days after application of composition | | |
|---|---|---|
| Dose 1 ml | Dose 2.5 ml | Control |
| 100 animals | 100 animals | 215 animals |
| 25 animals + | 41 animals + | 112 animals + |
| 6 additional animals were culled for slaughter | 3 additional animals were culled for slaughter | 42 additional animals were culled for slaughter |

The efficacy of treatment with doses of 1 ml was about 70% and with doses of 2.5 ml was about 53%. 154 animals (about 72%) from the control group were with clinical symptoms of DD, ID and IP. This investigation demonstrates prophylactic treatment of animals with a dose of 1.0 ml. Duration of immunity was about 5.5 month.

EXAMPLE 27

Treatment of cows against DD, ID and IP was done. Prophylactic application of a composition prepared in accordance with Example 14: intramuscular, 2 times in a dose of 5 ml with an interval of 10 days.

Summary of Investigation:

| Animals in-group 1 were treated Observation before the treatment | |
|---|---|
| Amount of animals/clinical manifestations of DD, ID and IP 160 to 175 days after last treatment | 100/100 |
| Amount of animals/amount of limbs with lameness | 100/10 |
| Amount of healthy animals | 90 |
| Efficacy of treatment | 90% |
| Animals in group 2 were treated with placebo (control) Observation before treatment | |
| Amount of animals/clinical manifestations of DD, ID and IP 160 to 175 days after last application of placebo | 100/100 |
| Amount of animals/amount of animals with manifestations of Clinical symptoms of DD, ID and IP | 100/48 |
| Amount of healthy animals | 52 |
| Amount of ill animals during of observation time | 48% |

All animals of the control group (placebo) with clinical symptom of diseases were treated with local application of aseptic medicine or antibiotics. In case of IP the intramuscular injection of antibiotics was used.

EXAMPLE 28

Cows with clinical evidence of lameness and lesions of the interdigital space, which are typical for DD, ID and IP, were treated with various compositions. The composition was administered by intramuscular injection two times at one site with an interval of 10 days. The dose of the composition was 5 ml for each application.

The results are shown in Table 9.

| No of group | Composition as prepared in example | No of animals | Frequency of drug administration | Amount of healthy animals | |
|---|---|---|---|---|---|
| | | | | In 30-35 days after the first application | In 53-55 days after the first application |
| 1 | 14 | 10 | 2 | 10 | 10 |
| 2 | 15 | 10 | 2 | 9 | 9 |
| 3 | 18 | 10 | 2 | 10 | 10 |
| 4 | Control - treated by common methods | 10 | — | 3 | 5 |

EXAMPLE 29. HYDRO-COLLOIDS

Chemical nomenclature: Chitosan-Valeric acid-Hydro-Colloid

Subtitle: Polyaminosugar-Valeric acid-Hydrocomplex

Structural formula:

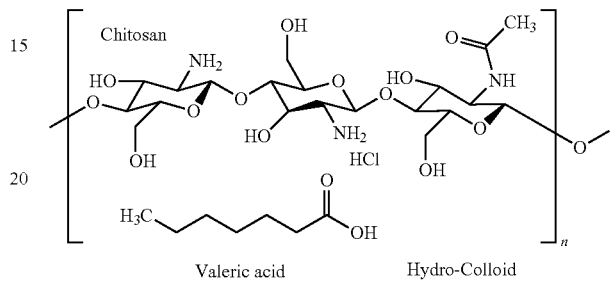

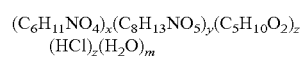 Chemical formula:

General Properties

Molecular weight: $x^*(161)+y^*(203)+z^*(102)+z^*(36.5)+m^*(18)$

Appearance: natural white to yellowish viscous liquid with typical odor

Solubility: soluble in: Water

Odor: typical, similar to Valeric acid

Density: 1.002 pH-value: 5.5

Storage: Keep protected from light; store in a container protected from air in a refrigerator at 4°-8° C.

Stability: 36 months under conditions described above

Chemical nomenclature: Chitosan-4-Aminobenzoic acid-Hydro-Colloid

Subtitle: Polyaminosugar-p-Aminobenzoic acid-Hydrocomplex

Structural formula:

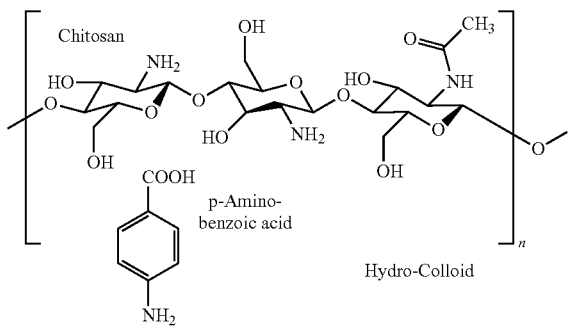

Chemical formula: $(C_6H_{11}NO_4)_x(C_8H_{13}NO_5)_y(C_7H_7NO_2)_z(H_2O)_m$

General Properties
  Molecular weight: $x*(161)+y*(203)+z*(137.14)+m*(18)$
  Appearance: Yellowish to yellow viscous liquid
  Chemical nomenclature: Chitosan-Glucuronic acid-Hydro-Colloid
  Subtitle: Polyaminosugar-Glucuronic acid-Hydrocomplex
  Structural formula:

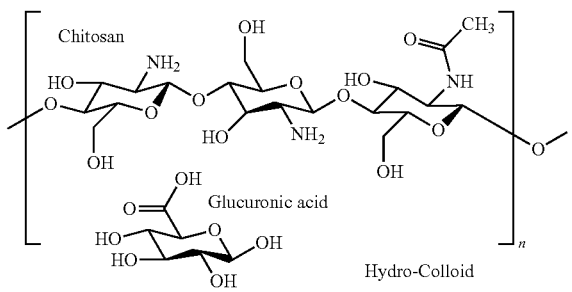

Chemical formula: $(C_6H_{11}NO_4)_x(C_8H_{13}NO_5)_y(C_6H_{10}O_7)_z(H_2O)_m$

General Properties
  Molecular weight: $x*(161)+y*(203)+z*(194.14)+m*(18)$
  Appearance: Yellowish to yellow viscous liquid

EXAMPLE 30. MANUFACTURING OF CHITOSAN-VALERIC ACID-HYDRO-COLLOID

Purification of Chitosan 80/100 and 80/200, AS-No.: 9012-76-4,
Amino-N-acetyl-D-glucosamine is sterilized in a separate vessel and is carried out to obtain Chitosan in pharmaceutical quality.
Reagent Solution
Sterile Amino-N-acetyl-D-glucosamine is resuspended under stirring for 15 minutes in this sterile water. 400 ml of Acetic acid is added to suspension under stirring (24 h) until a clear solution is obtained.
Purification Step
To this solution the 4 N Sodium hydroxide solution is added drop by drop (carefully) to obtain a pH 8.0 to 8.5. The resulting solution precipitates to a white mass. The obtained suspension is stirred not less than 30 minutes. The residue is separated from the liquid phase by filtration.
Resuspension
The precipitate is resuspended in an equal amount of purified (sterile) water (water for injection (Pharm. Eur.)) (401, initial amount). 80 ml of Pentanoyl chloride is measured. Under stirring conditions the Pentanoyl chloride is added drop by drop to the suspension. The obtained suspension is stirred until the solution is clear. 1.6 g Thiomersal is added (40 m/mL). The clear solution is the active ingredient (Hydro-Colloid). The obtained polysaccharide colloid (CVHC) is stored under 4° C. to 8° C. For an end product a aqueous solution is done with defined biological activity.
Overview of the Reaction Steps of Manufacturing
1. Chitosan+water→suspension
  suspension+HAc (24 h)→Chitosan-HAc-solution
2. Purification step
2.1. Chitosan-HAc-solution+4N NaOH→(pH 8-8.5) Chitosan+NaAc+$H_2O$
2.2. Chitosan+NaAc+$H_2O$→$H_2O$+NaAc
  →Chitosan (solid, purified)
3. Production
Chitosan (solid)+$H_2O$+Pentanoylchlorid→
Chitosan+Valeric acid+$H_2O$+HCl→CVHC (Chitosan-Valeric acid-Hydro-Colloid)

The production is a combination of a purification step of the basic material Chitosan and in process reaction with the second reagent Pentanoyl chloride.
This first critical step is the precipitation of Chitosan to obtain the total amount of the purified chitosan in pharmaceutical quality.
In process control: The reaction time and the pH-value are monitored to get a quantitative precipitation.
Test for the pharmaceutical quality of chitosan:
Test for the quality of the intermediate (Chitosan pharm quality)
Solubility in water: A sample of about 250 mg of the precipitate of Chitosan is resuspended in 1 ml of purified water
Target: No solubility can be obtained
Quality: is fulfilled if no reduction of the amount of the solid material can be detected.
Solubility in stronger acids: In parallel same amount of precipitate is suspended in 1 ml HCl (3N)
Target: Total solution
Quality: is fulfilled if a solution of the total amount of the solid material can be detected.
The second critical step is the dissolution process to the active ingredient. The control is done visually: The total amount of the precipitate should be solubilized.

EXAMPLE 31. EXAMINATION ON IDENTITY BY USING UV/VIS-SPECTROSCOPY

Test method according to EUROPEAN PHARMACOPOEIA 2.2.25 was used.
  Apparatus: Spectrophotometer Jasco 7800
  Conditions of measurement: Bandwidth 2 nm
  Range 200-600 nm
  Blank correction with solvent
  Temperature: 25° C.
  UV-Cell: 12.5×45 mm semi-micro, 10 mm path length
    UV-grade silica
  Solvent: $H_2O$
  Test solution: An adequate sample of Chitosan HCl, Chitosan-HAc, Chitosan, Chitosan-Valeric acid-Hydro Colloid and valeric acid, respectively was dissolved in the solvent above. This mixture was shacked and afterwards sonified in an ultrasonic bath for 5 min.
The absorption maxima according to the general fundamentals of spectroscopy and the chemical structure with specific chromophore groups and substituents can be expected at: 200 nm for Chitosan HCl, Chitosan-HAc, Chitosan-Valeric acid-Hydro Colloid and valeric acid, respectively

| UV-Maximum | Chitosan HCl | Chitosan HAc | Chitosan | CVHC | Valeric acid |
|---|---|---|---|---|---|
| nm | 200 | 200 | — | 200 | 211 |

The absorption maxima of Chitosan could not be analysed since Chitosan is a water insoluble solid, which can also not be solubilized in typical organic solvents.

The comparison of all spectra show no significance or structural modification like aromatic bonds etc. Based on the measured spectra and literature data of the raw materials the measured spectrum corresponds to prospected spectra. Thus, the measured data above confirm the identity of the prospected structure.

EXAMPLE 32: IR-ABSORPTION SPECTROPHOTOMETRY

Test method according to EUROPEAN PHARMACOPOEIA 2.2.24 was used.

For identification of the active principle Chitosan-Valeric acid-Hydro-Colloid a series of IR-spectra of different Chitosan-Derivates are compared with the spectrum of the product and of Valeric acid.

1. Method and Parameters
   Apparatus Infrared-Spectrometer FT/IR 410 Jasco
   Range: 4000 cm$^{-1}$ to 600 cm$^{-1}$
   Test sample: A mixture of 4.8 mg of Chitosan, or a mixture of 4 mg of Chitosan-HCl or a mixture of 3.8 mg of Chitosan Acetate and 100 mg KBr is carefully grinded and pressed to a suitable potassium bromide disk, or a film of Chitosan-Valeric acid-Hydro Colloid or NaCl plate for valeric acid
   Conditions of Measurement:
   Background correction: actual
   Temperature 20° C.
   The measured spectrum corresponds directly to the literature spectra from database.
   Result: The measured data above confirms the identity of the tested substances.
2. Data of the Different IR-Spectra

| Chitosan-Base | Chitosan-HCl | Chitosan-HAc | Dried Chitosan-valeric acid Colloid | Valeric acid |
|---|---|---|---|---|
| 3398 | 3365 | 3424 | 3426 | |
| 2919/2875 | 2887 | 2926/ | 2960-2872 | 2960-2875 |
| | | | | 2673 |
| | 2018 | 2092 | 2130 | |
| | | 1708 | | 1717 |
| 1665 | | | | |
| 1596 | 1606 | | | |
| 1562 | | 1561 | 1569 | |
| | 1509 | | | |
| | | | | 1467/1456 |
| 1421 | 1410 | 1408 | 1424 | 1413 |
| 1377 | 1380 | | | 1381 |
| 1320 | 1320 | 1336 | 1315 | |
| | | | | 1279 |
| 1256 | 1246 | 1254 | 1236 | 1215 |
| 1154 | 1155 | 1155 | 1154 | |
| 1079/1032 | 1084 | 1089 | 1076-1013 | 1109 |
| 897 | 896 | 890 | 926 | 940 |

The IR signals of Valerie acid in the active principle are very small to not visible.

Comparison to literature data: Based on the measured spectra and literature data of the raw materials, the measured spectrum of CVHC corresponds to prospected spectrum.

Result: The measured data above confirm the identity of the proposed structure.

EXAMPLE 33. $^{13}$C-NMR-SPECTROSCOPY ANALYSIS

Test method according to EUROPEAN PHARMACOPOEIA 2.2.33 was used.

a) 13C-NMR-Spectrum of Chitosan
1. Method and Parameters
   Apparatus Bruker AMX 500 AVANCE
   Conditions of measurement
   Scan frequency: 125 MHz for Chitosan, Chitosan HCl, Chitosan HAc, Glucosamin HCl, N-Acetylglucosamin, Chitosan-Valeric acid-Hydro-Colloid, Valerie acid
   Temperature: 300 K for Chitosan, Chitosan HCl, Chitosan HAc, Chitosan-Valeric acid-Hydro-Colloid, Valerie acid; 301 K for Glucosamin HCl and N-Acetylglucosamin
   Solvent: D$_2$O for Chitosan, Chitosan HCl, Chitosan HAc, Glucosamin HCl, N-Acetylglucosamin;
   DMSO-D6 for Chitosan-Valeric acid-Hydro-Colloid
   CDCl$_3$ for Valerie acid
   Concentration: —for Chitosan, Chitosan HCl, Chitosan HAc, Chitosan-Valeric acid-Hydro-Colloid;
   approx. 15 mg/0.5 ml for Glucosamin HCl, N-Acetylglucosamin and Valerie acid
   Calibration: —for Chitosan, Chitosan HCl, Chitosan HAc, Glucosamin HCl, N-Acetylglucosamin
   DMSO-D6 for Chitosan-Valeric acid-Hydro-Colloid
   CDCl$_3$ for Valerie acid
2. Results
a) $^{13}$C-NMR-Spectroscopy Analysis of Chitosan
   Measurement in solution: According to the missing solubility in neutral solvents a measurement in solution is not possible.
   Measurement in solid state: A measurement in solid state was not possible. Also after long measurement conditions (time) no acceptable signals appeared.
   Result: NMR-Identification of Chitosan is not possible.
b) $^{13}$C-NMR-Spectroscopy Analysis of Chitosan HCl

| Results | [d] | Classification (Carbon number) |
|---|---|---|
| | 97.67 | C1 |
| | 76.41/74.80 | C5 |
| | 70.28 | C3 |
| | 64.41 | C4 |
| | 60.11 | C6 |
| | 56.06 | C2 |

| | | [ppm] |
|---|---|---|
| Target | The following characteristic chemical shifts according to the general fundamentals of spectroscopy and the chemical skeleton with substituents can be expected at: | 100 70 56 |

General Literature: Hesse, Meier, Zeeh Spektr. Methoden Thieme Verlag 5. Auflage Result: The measured data above confirms the identity of the tested substance.

c) $^{13}$C-NMR-Spectroscopy Analysis of Chitosan HAc

| Results | [d] | Classification (Carbon number) |
|---|---|---|
| Glucosamine | 98.39 | C1 |
| skeleton | 74.79 | C5 |
|  | — | C3 |
|  | — | C4 |
|  | — | C6 |
|  | — | C2 |
| Acetic Acid | 23.82 | CH$_3$ |
|  | 180.31 | >C=O |

[ppm]

| | | |
|---|---|---|
| Target | The following characteristic chemical shifts according to the general fundamentals of spe spectroscopy and the chemical skeleton with substituents can be expected at: | 98.39 23.82 180.31 |

General Literature: Hesse, Meier, Zeeh Spektr. Methoden Thieme Verlag 5. Auflage Result: The measured data above confirms the identity of the tested substance.

d) $^{13}$C-NMR-Spectroscopy Analysis of Glucosamin HCl

| Results | [d] | Classification (Carbon number) |
|---|---|---|
|  | 92.94/89.34 | C1 |
|  | 76.25 | C5 |
|  | 72.28/71.69 | C3 |
|  | 69.85/69.77 | C4 |
|  | 60.66/60.51 | C6 |
|  | 54.62/57.08 | C2 |

[ppm]

| | | |
|---|---|---|
| Target | The following characteristic chemical shifts according to the general fundamentals of spectroscopy and the chemical skeleton with substituents can be expected at: | 92.94/89.34 60.66/60.51 54.62/57.08 |

General Literature: Hesse, Meier, Zeeh Spektr. Methoden Thieme Verlag 5. Auflage Comparison to literature data: The measured spectrum corresponds directly to the literature spectra from database.

Result: The measured data above confirms the identity of the tested substance.

e) $^{13}$C-NMR-Spectroscopy Analysis of N-Acetylglucosamin

| Results | [d] | Classification (Carbon number) |
|---|---|---|
|  | 95.06/90.95 | C1 |
|  | 76.01/74.08 | C5 |
|  | 71.64/70.86 | C3 |
|  | 70.22/69.99 | C4 |
|  | 60.89/60.74 | C6 |
|  | 56.90/54.26 | C2 |
|  | 22.29/22.03 | CH$_3$ |
|  | 174.85/174.59 | C=O |

| | | |
|---|---|---|
| Target | The following characteristic chemical shifts according to the general fundamentals of spectroscopy and the chemical skeleton with substituents can be expected at: | 95.06/90.95 22.29/22.03 174.85/174.59 |

General Literature: Hesse, Meier, Zeeh Spektr. Methoden Thieme Verlag 5. Auflage Result: The measured data above confirms the identity of the tested substance.

f) $^{13}$C-NMR-Spectroscopy Analysis of Chitosan-Valeric Acid-Hydro-Colloid

| Results | [d] | Classification (Carbon number) |
|---|---|---|
| Glucosamine | 100.95 | C1 |
| skeleton | 78.57 | C5 |
|  | 76.10 | C3 |
|  | 73.10 | C4 |
|  | 61.40 | C6 |
|  | 57.57 | C2 |
| Valeric acid | 180.66 | C5' |
|  | 29.23 | C4' |
|  | 24.85 | C3' |
|  | 23.37 | C2' |
|  | 14.87 | C1' |

[ppm]

| | | |
|---|---|---|
| Target | The following characteristic chemical shifts according to the general fundamentals of spectroscopy and the chemical skeleton with substituents can be expected at: | 100.95 61.40 57.57 180.66 14.87 |

General Literature: Hesse, Meier, Zeeh Spektr. Methoden Thieme Verlag 5. Auflage Result: The measured data above confirms the identity of the proposed structure.

g) $^{13}$C-NMR-Spectroscopy Analysis of Valeric Acid

| Results | [d] | Classification (Carbon number) |
|---|---|---|
|  | 180.5 | C5 |
|  | 33.8 | C4 |
|  | 26.7 | C3 |
|  | 22.2 | C2 |
|  | 10.6 | C1 |

[ppm]

| | | |
|---|---|---|
| Target | The following characteristic chemical shifts according to the general fundamentals of spectroscopy and the chemical skeleton with substituents can be expected at: | 180 10.6 |

General Literature: Hesse, Meier, Zeeh Spektr. Methoden Thieme Verlag 5. Auflage Comparison to literature data: The measured spectrum corresponds directly to the literature spectra from database.

Result: The measured data above confirms the identity of the tested substance.

3. Comparison of the NMR Spectra

| Chitosan HCl | Chitosan HAc | Glucosamin HCl | N-Acetyl-glucosamin | Chitosan-Valeric acid-Hydro- | Valeric acid | Classification (Carbon number) |
|---|---|---|---|---|---|---|
| 97.7 | 98.4 | 92.9/89.3 | 95.0/91.0 | 101.0 | | C |
| 56.1 | | 54.6/57.1 | 54.3/56.9 | 57.6 | | C |
| 70.3 | | 71.7/72.3 | 71.6/70.9 | 76.1 | | C |
| 64.4 | | 69.9/69.8 | 70.2/70.0 | 73.1 | | C |
| 76.4/74.8 | 74.8 | 7 | 76.0/74.1 | 78.6 | | C |
| 60.1 | | 60.5/60.7 | 60.9/60.7 | 61.4 | | C |
| | 22.7 | | | | | |
| | 23.8 | | | | | |
| | 180.3 | | 174.9/174.6 | | | |
| | | | | 14.9 | 13.0 | |
| | | | | 23.4 | 22.0 | |
| | | | | 24.9 | 26.0 | |
| | | | | 29.2 | 33. | |
| | | | | 108.7 | 180. | |
| Literature | — | — | X | — | — | X |

Comparison to literature data: Not available or Based on the measured spectra and literature data of the raw materials, the measured spectrum corresponds directly to prospected spectra.

Result: The measured data above confirm the identity of the proposed structure.

EXAMPLE 34. TLC-METHOD FOR THE ANALYSIS OF CHITOSAN AND IMPURITIES IN THE NEW PRODUCT CHITOSAN-VALERIC ACID-HYDRO-COLLOID (CVHC)

Test method according to EUROPEAN PHARMACOPOEIA 2.2.27 was used.

This part presents the procedures and data of thin layer chromatography for the identification of CVHC along with the Rf values in the used solvent mixtures and spot colors when detected under UV-light (365 nm and 254 nm), visible light and with typical visualisation reagents.

The original based raw material for any kind of glucosamines is the natural material Chitin from insects or crabs. The monomeric structure of these biopolymers is N-Acetyl-Glucosamine.

For pharmaceutical and other use in most cases deacetylated Chitin is typical. This resulting biopolymer is the so called Chitosan, which can be modified into water soluble ionic compounds. The monomeric structure of this Chitosan should be theoretically Glucosamine. Because the deacetylation step does not run totally, Chitosan has a mixed structure of N-Acetyglucosamine (acetylated) and Glucosamine (deacetylated) units. Chitosan-Valeric acid-Hydro-Colloid is a new Polyaminosugar-valeric acid hydrocomplex. Therefore no positive analytical test results for N-Acetyl-Glucosamine and Glucosamine should be possible. If monomeric fragments are embedded as residual impurities, it should be possible to identify Chitosan in form of its water soluble ionic compounds Chitosan HCl and Chitosan HAc.

1. Method

| Apparatus | Camag Chromatographic Tank System |
|---|---|
| TLC-plate | Merck Si 60 F 254 precoated plates |
| Conditions | Protected from sunlight and with chamber saturation |
| Temperature | 20-25° C. |
| Development: | Vertical development |

Chromatographic Conditions

| Sample-solution | See the single analytes |
|---|---|
| Application | 30 μl |
| Drying | Min. 2 minutes in an air-stream |
| Motion range | 80 mm |

Mobile Phase

| Solvents | Acetone | Water | 25% aq. Ammonia | — |
|---|---|---|---|---|
| Mixture | 20 | 10 | 5 | — |

2. Analysis and Results a) Chitosan

Sample Preparation

Sample: Chitosan suspended in water

1) Apparatus: reflux condensor

Conditions: heating for about 30 minutes under reflux (145° C.)

2) Apparatus: Ultra sonic bath

Conditions: Sonification for about 30 minutes at 45° C.

3) Apparatus: reflux condensor

Conditions: heating for about 30 minutes under reflux (145° C.)

4) Filtration: 0.45 μm filter

The clear filtrate was used for analysis.

Detection with UV-Fluorescence and VIS

| Fluorescence wavelength | 254 nm | 365 nm | VIS |
|---|---|---|---|
| Compound signal | No | No | No |
| Impurities | No | No | No |

Detection with Visualisation Reagents

| Visible light | Group specific reagent 1 | Group specific reagent 2 | Anisaldehyde-Sulfuric acid reagent | Iodine |
|---|---|---|---|---|
| Compound signal | No | No | No | No |
| Impurities | No | No | No | No |

-continued

| Visible light | Group specific reagent 1 | Group specific reagent 2 | Anisaldehyde-Sulfuric acid reagent | Iodine |
|---|---|---|---|---|
| | Group specific reagent 1: Naturstoff-Reagent/DT/366 nm | | | |
| | Group specific reagent 2: 5% Ninhydrine/EtOH | | | |
| Rf-value | No signal for chitosan can be identified | | — | |
| | Non specified impurities: | | | Not detected |

Alternative: Solubilization in organic solvents show equal results because of the missing solubility of Chitosan.

Result: An acceptable solution of Chitosan in waterish or organic solvents like Methanol etc. is not possible. A suitable solubilization of Chitosan is only possible in stronger acids like HCl or HAc under production of Chitosan HCl or Chitosan HAc.

b) Chitosan HCl 5 mg Chitosan HCl/ml $H_2O$ was used for analysis.
Detection with UV-Fluorescence and VIS

| Fluorescence wavelength | 254 nm | 365 nm | VIS |
|---|---|---|---|
| Compound signal | No | No | No |
| Impurities | No | No | No |

Detection with Visualisation Reagents

| Visible light | Group specific reagent 1 | Group specific reagent 2 | Anisaldehyde-Sulfuric acid reagent | Iodine |
|---|---|---|---|---|
| Compound signal | No | No | Grey spot | Brown spot |
| Impurities | No | No | No | No |
| Group specific reagent 1: Naturstoff-Reagent/DT/366 nm | | | | |
| Group specific reagent 2: 5% Ninhydrine/EtOH | | | | |
| Rf-value | Chitosan HCl | | 0.0 | |
| | Non specified impurities: | | | Not detected |
| Target | Compound purity | | One main spot | |
| | Anisaldehyd-Sulfuric acid-reagent respectively Iodine as non-selective reagents for detection of non-specified impurities should show no greater impurities | | | |
| | A relative retardation factor (Rf) of this compound according to the chemical skeleton under this described chromato-graphic conditions for such an polymer can be expected at: | | | |
| | 0.0 | | — | — |

Result: Compound purity; One main spot.

c) Chitosan HAc 5 mg Chitosan HAc/ml $H_2O$ was used for analysis.
Detection with UV-Fluorescence and VIS

| Fluorescence wavelength | 254 nm | 365 nm | VIS |
|---|---|---|---|
| Compound signal | No | No | No |
| Impurities | No | No | No |

Detection with Visualisation Reagents

| Visible light | Group specific reagent 1 | Group specific reagent 2 | Anisaldehyde-Sulfuric acid reagent | Iodine |
|---|---|---|---|---|
| Compound signal | No | No | Grey spot | Brown spot |
| Impurities | No | No | No | No |
| Group specific reagent 1: Naturstoff-Reagent/DT/366 nm | | | | |
| Group specific reagent 2: 5% Ninhydrine/EtOH | | | | |
| Rf-value | Chitosan HAc | | 0.0 | |
| | Non specified impurities: | | | Not detected |
| Literature Value | Not available data from | | — | |
| Target | Compound purity | | One main spot | |
| | Anisaldehyd-Sulfuric acid-reagent respectively Iodine as non-selective reagents for detection of non-specified impurities should show no greater impurities | | | |
| | A relative retardation factor (Rf) of this compound according to the chemical skeleton under this described chromatographic conditions for such an polymer can be expected at: | | | |
| | 0.0 | | — | — |

Result: Compound purity; One main spot.

d) Glucosamine HCl 5 mg Glucosamine HCl/ml $H_2O$ was used for analysis.
Detection with UV-Fluorescence and VIS

| Fluorescence wavelength | 254 nm | 365 nm | VIS |
|---|---|---|---|
| Compound signal | No | No | No |
| Impurities | No | No | No |

Detection with Visualisation Reagents

| Visible light | Group specific reagent 1 | Group specific reagent 2 | Anisaldehyde-Sulfuric acid reagent | Iodine |
|---|---|---|---|---|
| Compound signal | Blue spot | Red spot | Grey spot | Brown spot |
| Impurities | No | No | No | No |
| Group specific reagent 1: Naturstoff-Reagent/DT/366 nm | | | | |
| Group specific reagent 2: 5% Ninhydrine/EtOH | | | | |
| Rf-value | Glucosamine HCl | | 0.67 | |
| | Non specified impurities: | | | Not detected |
| Literature Value | Not available data from | | — | |
| Target | Compound purity | | One main spot | |
| | Anisaldehyd-Sulfuric acid-reagent respectively Iodine as non-selective reagents for detection of non-specified impuritieshould show no greater impurities | | | |
| | A relative retardation factor (Rf) of this compound according to the chemical skeleton under this described chromato-graphic conditions can be expected between | | | |
| | 0.6 | and | 0.8 | |

Result: Compound purity; One main spot.

e) N-Acetylglucosamine
5 mg N-Acetylglucosamine/ml H$_2$O was used for analysis
Detection with UV-Fluorescence and VIS

|  | Fluorescence wavelength | | |
| --- | --- | --- | --- |
|  | 254 nm | 365 nm | VIS |
| Compound signal | No | No | No |
| Impurities | No | No | No |

Detection with Visualisation Reagents

| Visible light | Group specific reagent 1 | Group specific reagent 2 | Anisaldehyde-Sulfuric acid reagent | Iodine |
| --- | --- | --- | --- | --- |
| Compound signal | Blue spot | No | Grey spot | Brown spot |
| Impurities | No | No | No | No |

Group specific reagent 1: Naturstoff-Reagent/DT/366 nm
Group specific reagent 2: 5% Ninhydrine/EtOH

| Rf-value | N-Acetylglucosamine | 0.72 |
| --- | --- | --- |
|  | Non specified impurities: | Not detected |
| Target | Compound purity | One main spot |

Anisaldehyd-Sulfuric acid-reagent respectively Iodine as non-selective reagents for detection of non-specified impurities should show no greater impurities
A relative retardation factor (Rf) of this compound according to the chemical skeleton under this described chromato-graphic conditions can be expected between 0.6 and 0.8

Result: Compound purity; One main spot.

f) Chitosan-Valeric acid-Hydro-Colloid (CVHC)
CVHC is a high viscous waterish gel. Two drops of CVHC was used for analysis.
Detection with UV-Fluorescence and VIS

|  | Fluorescence wavelength | | |
| --- | --- | --- | --- |
|  | 254 nm | 365 nm | VIS |
| Compound signal | No | No | No |
| Impurities | No | No | No |

Detection with Visualisation Reagents

| Visible light | Group specific reagent 1 | Group specific reagent 2 | Anisaldehyde-Sulfuric acid reagent | Iodine |
| --- | --- | --- | --- | --- |
| Compound signal | No | No | Grey spot | Brown spot |
| Impurities | No | No | No | No |

Group specific reagent 1: Naturstoff-Reagent/DT/366 nm
Group specific reagent 2: 5% Ninhydrine/EtOH

| Rf-value | Chitosan-Valeric acid-Hydro-Colloid | 0.0 |
| --- | --- | --- |
|  | Non specified impurities: | Not detected |
| Literature Value | Not available data from | — |
| Target | Compound purity | One main spot |

Anisaldehyd-Sulfuric acid-reagent respectively Iodine as non-selective reagents for detection of non-specified impurities should show no greater impurities
A relative retardation factor (Rf) of this compound according to the chemical skeleton under this described chromato-graphic conditions for such an polymer can be expected at:
0.0 — —

Result: Compound purity; One main spot.

g) Valeric Acid
1 µl Valeric acid (pure) was used for analysis.
Detection with UV-Fluorescence and VIS

|  | Fluorescence wavelength | | |
| --- | --- | --- | --- |
|  | 254 nm | 365 nm | VIS |
| Compound signal | No | No | No |
| Impurities | No | No | No |

Detection with Visualisation Reagents

| Visible light | Group specific reagent 1 | Group specific reagent 2 | Anisaldehyde-Sulfuric acid reagent | Iodine |
| --- | --- | --- | --- | --- |
| Compound signal | No | No | No | Yellow spot |
| Impurities | No | No | No | No |

Group specific reagent 1: Naturstoff-Reagent/DT/366 nm
Group specific reagent 2: 5% Ninhydrine/EtOH

| Rf-value | Valeric acid | 0.0 |
| --- | --- | --- |
|  | Non specified impurities: | Not detected |
| Literature Value | Not available data from | — |
| Target | Compound purity | One main spot |

Anisaldehyd-Sulfuric acid-reagent respectively Iodine as non-selective reagents for detection of non-specified impurities should show no greater impurities
A relative retardation factor (Rf) of this compound according to the chemical skeleton under this described chromato-graphic conditions can be expected between
0.0 — —

Result: Compound purity; One main spot.

3. Comparison of the Results of the TLC Analysis

|  | Chitosan | Chitosan HCl | Chitosan HAc | Glucosamine HCl | N-Acetyl-glucoamine HCl | Chitosan-Valerie colloid | Valerie acid |
| --- | --- | --- | --- | --- | --- | --- | --- |
| Rf-value | Not possible | 0 | 0 | 0.67 | 0.72 | 0 | 0 |
| Detection |  |  | Compound signal |  |  |  |  |
| UV 254 nm | — | — | — | — | — | — | — |
| UV 365 nm | — | — | — | — | — | — | — |
| Visible light | — | — | — | — | — | — | — |
| Naturstoff-Reagent | — | — | — | Blue spot | Blue spot | — | — |

|  | Chitosan | Chitosan HCl | Chitosan HAc | Gluco-samine HCl | N-Acetyl-glucoamine HCl | Chitosan-Valerie colloid | Valerie acid |
|---|---|---|---|---|---|---|---|
| Ninhydrine Reagent | — | — | — | Red spot | — | — | — |
| Anisalde-hyde-Sulfuric acid reagent | — | Grey spot | Grey spot | Grey spot | Grey spot | Grey spot | — |
| Iodine Reagent | — | Brown spot | Brown spot | Brown spot | Brown spot | Brown spot | Yellow Spot |

The results above from TLC show that there is no evidence of monomeric or dimeric structure which could be detected with the specific derivation reagents tested above. The detection and the Rf value of "0" show the similarity of Chitosan-Valeric acid-Hydro-Colloid to the related compounds Chitosan HCl and Chitosan HAc. A specific identification of Valeric acid with this TLC-System failed. Chitosan-Valeric acid-Hydro-Colloid can only be a Poly-Amino-sugar-colloid, but not a solution of Chitosan or a Chitosan derivate with Valeric acid in water.

EXAMPLE 35. TLC-METHOD FOR THE ANALYTICAL DETECTION OF VALERIC ACID IN CHITOSAN-VALERIC ACID-HYDRO-COLLOID

1. Method and Parameters

A new TLC system was established for a identification and purity testing of the constituent Valeric acid.

| | |
|---|---|
| Apparatus | Camag Chromatographic Tank System |
| TLC-plate | Merck Si 60 F. 254 precoated plates |
| Conditions | Protected from sunlight and with chamber saturation |
| Temperature | 20-25° C. |
| Development: | Vertical development |

Chromatographic Conditions

| | |
|---|---|
| Drying | Min. 2 minutes in an air-stream |
| Motion range | 80 mm |

Mobile Phase

| Solvents | Ethyl Acetate | — | — | — |
|---|---|---|---|---|
| Mixture | 100 | — | — | — |

2. Results a) Valeric Acid (Pure)

2 µl of Valeric acid (pure) was used for analysis.

Detection with UV-Fluorescence and VIS

| | Fluorescence wavelength | | |
|---|---|---|---|
| | 254 nm | 365 nm | VIS |
| Compound signal | No | No | No |
| Impurities | No | No | No |

Detection with Visualisation Reagents

| Visible light | Group specific reagent | Anisaldehyde-Sulfuric acid reagent | Iodine |
|---|---|---|---|
| Compound signal | Yellow spot/blue background | Pink spot | Yellowish spot |
| Impurities | No | No | No |
| Group specific reagent: Bromcresol Green/Bromphenol Blue/Potassium Permanganate Reagent [Jork et al.] | | | |
| Rf-value | Valeric acid | | 0.56 |
| | Non specified impurities: | | Not detected |
| Literature Value | Not available | data from | — |

Detection limit: of valeric acid with this visualisation reagent after TLC-chromatography: 0.03 µg b) Chitosan-Valeric Acid-Hydro-Colloid (CVHV)

45 µl Chitosan-Valeric acid-Hydro-Colloid, pure (this is an about 850 times higher amount of valeric acid, compared with the tests before) was used for analysis.

Detection with UV-Fluorescence and VIS

| | Fluorescence wavelength | | |
|---|---|---|---|
| | 254 nm | 365 nm | VIS |
| Compound signal | No | No | No |
| Impurities | No | No | No |

Detection with Visualisation Reagents

| Visible light | Group specific reagent | Anisaldehyde-Sulfuric acid reagent | Iodine |
|---|---|---|---|
| Compound signal | Blue spot/blue background | Grey spot | Brown spot |
| Impurities | No | No | No |
| Group specific reagent: Bromcresol Green/Bromphenol Blue/Potassium Permanganate Reagent [Pork et al.] | | | |
| Target | Compound purity | One main spot | |
| | Anisaldehyd-Sulfuric acid-reagent respectively Iodine as non-selective reagents for detection of non-specified impurities should show no greater impurities | | |
| | The Group specific reagent Bromcresol Green/Bromphenol Blue/Potassium Permanganate Reagent should show typical results for the compounds | | |
| | A relative retardation factor (Rf) of this compound according to the chemical skeleton under this described chromatographic conditions can be expected at | | |
| | 0.0 | for Chitosan-derivatives | |
| | appr. 0.6 | for valeric acid if available | |
| Rf-value | Chitosan-Valeric acid-Hydro-Colloid | | 0.0 |
| | Non specified impurities: | | Not detected |
| Rf-value | Valeric acid | | Not detected |
| | Non specified impurities: | | Not detected |
| Literature Value | Not available | data from | — |

Detection limit of valeric acid with this visualisation reagent after TLC-chromatography: 0.03 µg Pure Valeric acid can be identified with this TLC-System. Colloidal integrated Valeric acid can not be detected in the pure compound Chitosan-Valeric acid-Hydro-Colloid. The detection and the Rf value of "0" show the similarity of Chitosan-Valeric acid-Hydro-Colloid to other related Chitosan compounds. Chitosan-Valeric acid-Hydro-Colloid can only be a Poly-Amino-sugar colloid, but not a solution of Chitosan or a Chitosan derivate with Valeric acid in water. The results above confirm the identity of the proposed structure.

EXAMPLE 36. ELIMINATION OF VALERIC ACID FROM CHITOSAN-VALERIC ACID-HYDRO-COLLOID WITH HIGH VACUUM AND HIGHER TEMPERATURE

Method: Estimation of the loss on drying (special method)
Apparatus: Speed circulating vacuum concentrator
Conditions: 5 mbar
Temperature: 60° C.
Time: 1 week
End point: Constant mass
Appearance: Glassy mass
Result Odor: No typical odor from valeric acid
Sample Preparation
  Redissolution partly with water
  Appearance: High viscous gel
TLC-Analysis
  Apparatus: Camag Chromatographic Tank System
  TLC-plate: Merck Si 60 F 254 precoated plates
  Conditions: Protected from sunlight and with chamber saturation
  Temperature: 20-25° C.
  Development: Vertical development
Chromatographic Conditions
  Sample-solution See above
  Application: 5 µl
  Drying: Min. 2 minutes in an air-stream
  Motion range: 80 mm
  Mobile Phase

| Solvents | Ethyl Acetate | — | — | — |
|---|---|---|---|---|
| Mixture | 100 | — | — | — |

Detection with UV-Fluorescence and VIS

| | Fluorescence wavelength | | |
|---|---|---|---|
| | 254 nm | 365 nm | VIS |
| Compound signal | No | No | No |
| Impurities | No | No | No |

Detection with Visualisation Reagents

| Visible light | Group specific reagent | Anisaldehyde-Sulfuric acid reagent | Iodine |
|---|---|---|---|
| Compound signal | Blue spot/blue background | grey spot | brown spot |
| Impurities | No | No | No |
| Group specific reagent: Bromcresol Green/Bromphenol Blue/Potassium Permanganate Reagent [Jork et al.] | | | |
| Rf value | spot | | 0 |

Detection limit: of Valeric acid with this visualization reagent after TLC-chromatography: 0.03 µg Result: With high vacuum and higher temperature a disproportion of Chitosan-Valeric acid-Hydro-Colloid takes place. The elimination of Valeric acid can be shown by absolutely no typical odor from Valeric acid. The elimination of Valeric acid can be shown by TLC analysis: no typical spot of free valeric acid at Rf-value 0.56. Chitosan or Chitosan compounds can be identified at Rf-value 0. Chitosan-Valeric acid-Hydro-Colloid can only be a Poly-Amino-sugar-colloid, but not a solution of Chitosan or a Chitosan derivate with valeric acid in water.

EXAMPLE 37. DISPROPORTION OF CHITOSAN-VALERIC ACID-HYDRO-COLLOID WITH SOLVENTS

The structure of Chitosan-Valeric acid-Hydro-Colloid is decomposed in Ethyl acetate to Valeric acid and a Chitosan compound.
Sample Preparation
  Apparatus: separating funnel, evaporator
  Liquid-liquid distribution: 20 ml Chitosan-Valeric acid-Hydro-Colloid and 10 ml Ethyl acetate
  Conditions: Shaking for about 5 minutes and wait for phase separation
  Separation of phases: The ethyl acetate phase was collected
  Concentration step: The about 10 ml were concentrated to liquid residue (waterish) with an evaporator
  Resolubilization: in 1 ml Methanol
  Homogenization: Centrifugation step about 5 min 12.000 rpm
  Phase separation: Upper phase: clear methanolic solution
  Lower phase: high viscous gel
TLC Analysis of Upper and Lower Phase (See Above)
a) Analysis of upper phase (clear methanolic solution)
TLC-Analysis
  Apparatus: Camag Chromatographic Tank System
  TLC-plate: Merck Si 60 F 254 precoated plates
  Conditions: Protected from sunlight and with chamber saturation
  Temperature: 20-25° C.
  Development: Vertical development
Chromatographic Conditions
  Sample-solution: clear methanolic solution
  Application: 5 µl
  Drying: Min. 2 minutes in an air-stream
  Motion range: 80 mm
  Mobile Phase

| Solvents | Ethyl Acetate | — | — | — |
|---|---|---|---|---|
| Mixture | 100 | — | — | — |

Detection with UV-Fluorescence and VIS

| | Fluorescence wavelength | | |
|---|---|---|---|
| | 254 nm | 365 nm | VIS |
| Compound signal | No | No | No |
| Impurities | No | No | No |

Detection with Visualisation Reagents

| Visible light | Group specific reagent | Anisaldehyde-Sulfuric acid reagent | Iodine |
|---|---|---|---|
| Compound signal | Yellow spot/blue background | No | Light yellowish spot |
| Impurities | No | No | No |
| Group specific reagent: Bromcresol Green/Bromphenol Blue/Potassium Permanganate Reagent [Jork et al.] | | | |
| Rf-value | Valeric acid | | 0.57 |
| | Non specified impurities: | | — |

Detection limit with visualisation reagent: 0.03 µg

Result: The upper phase is a clear methanolic solution. Valeric acid can be identified after decomposition of the Hydro-Colloid in this solution with TLC. No Chitosan or Chitosan compound can be detected with TLC.

b) Analysis of Lower Phase (High Viscous Gel)

TLC-Analysis

Apparatus: Camag Chromatographic Tank System

TLC-plate: Merck Si 60 F 254 precoated plates

Conditions: Protected from sunlight and with chamber

Temperature: 20-25° C.

Development: Vertical development

Chromatographic Conditions

Sample-solution: high viscous gel, totally redissolved in water

Application: 30 µl

Drying: Min. 2 minutes in an air-stream

Motion range: 80 mm

Mobile Phase

| Solvents | Ethyl Acetate | — | — | — |
|---|---|---|---|---|
| Mixture | 100 | — | — | — |

Detection with UV-Fluorescence and VIS

| | Fluorescence wavelength | | |
|---|---|---|---|
| | 254 nm | 365 nm | VIS |
| Compound signal | No | No | No |
| Impurities | No | No | No |

Detection with Visualisation Reagents

| Visible light | Group specific reagent | Anisaldehyde-Sulfuric acid reagent | Iodine |
|---|---|---|---|
| Compound signal | Blue spot/blue background | Grey spot | Brown spot |
| Impurities | No | No | No |
| Group specific reagent: Bromcresol Green/Bromphenol Blue/Potassium Permanganate Reagent [Jork et al.] | | | |
| Rf-value | Spot | | 0 |
| | Non specified impurities: | | — |

Detection limit with visualisation reagent: 0.03 µg

Results: The lower phase is a high viscous gel, soluble in water. No Valeric acid can be detected in this phase by TLC. Chitosan or a Chitosan compound can be identified in the lower phase (gel) by TLC.

| Results from TLC analysis | A disproportion of Chitosan-Valeric acid-Hydro-Colloid is possible with typical solvents like Ethyl acetate and afterwards with Methanol |
|---|---|
| | A re-solubilization of from disproportioned Chitosan-Valeric acid-Hydro- Colloid can be realized with Methanol |
| | The decomposition of Chitosan-Valeric acid-Hydro-Colloid in Ethyl acetate shows two phases |
| | Upper phase — Lower phase |
| | Ethyl acetate phase — Aqueous Colloid residue |
| | After concentration the Ethyl acetate phase was redissolved in Methanol and results also two phases |
| | Upper phase — Lower phase |
| | clear methanolic solution — high viscous gel |
| | — This gel can be re-dissolved totally in water |
| | can be identified — No can be identified |
| | No Chitosan or Chitosan compound can be detected — Chitosan or a Chitosan compound can be detected |

Summary of the Results

| | | Valeric acid pure | Chitosan-Valeric Acid-Hydro-Colloid (pure CVHC) | Elimination of from CVHC with high vacuum | Chitosan-Valeric acid-Hydro-Colloid (decomposed with Ethyl acetate) | |
|---|---|---|---|---|---|---|
| | | | | | Upper phase (Methanol) | Lower phase (Water) |
| Rf-value | 0.56 | + | − | − | + | − |
| Rf-value | 0 | − | + | + | − | + |
| Detection | | | | Compound signal | | |
| UV 254 nm | | — | — | — | — | — |
| UV 365 nm | | — | — | — | — | — |
| Visible light | | — | — | — | — | — |
| Anisaldehyde-Sulfuric acid reagent | | Pink spot | Grey spot | Grey spot | — | Grey spot |
| Iodine reagent | | Yellowish spot | Brown spot | Brown spot | Light yellowish spot | Brown spot |
| Bromcresol Green Bromphenol Blue reagent | | Yellow spot | Blue spot | Blue spot | Yellow spot | Blue spot |

Result: Chitosan-Valeric acid-Hydro-Colloid can only be a Poly-Amino-sugar-colloid, but not a solution of Chitosan or a Chitosan derivate with valeric acid in water. The results above confirm the identity of the proposed structure.

EXAMPLE 38. ESTIMATION OF THE RELATIVE DENSITY

Because of the high viscosity of Chitosan-Valeric acid-Hydro-Colloid the estimation of the density is not possible with a density bottle/pycnometer according to Test method according to EUROPEAN PHARMACOPOEIA 2.2.5.

1. Test Method by Weighing

Apparatus: 250 ml volumetric flask

Balance: Sartorius MC 1 LC 2200S

Thermometer: Thermometer with graduation (min 0.5° C.) and a range not more than 60° C.

Results 1.001 $[d_{20}^{20}]$

The active principle is a hydrogel, so the theoretical density should be higher than 1.0. The measured data confirms the identity of the proposed substance.

2. Test Method with Hydrometer

Test method according to EUROPEAN PHARMACOPOEIA 2.2.5 was used.

Apparatus: 250 ml volumetric flask

Hydrometer: Widder 1573°, 20° C.-M100-DIN 12791 Klasse H

Thermometer with graduation (min 0.5° C.) and a range not more than 60° C.

Conditions of measurement: Temperature 20+/−0.5° C. with electronic thermostate

Results 1.002 $[d_{20}^{20}]$

The active principle is a hydrogel, so the theoretical density should be higher than 1.0. The measured data confirms the identity of the proposed substance.

EXAMPLE 39. SULPHATED ASH

The Test method according to EUROPEAN PHARMACOPOEIA 2.4.14 was used.

Testing

| | |
|---|---|
| Apparatus | Suitable crucible (porcelain or platinum) were ignited at 600 +/− 50° C. for 30 min in a "Muffel"-oven allow to cool in a desiccator over silica gel or other suitable desiccant Estimation of crucible weight |
| Weight | Weight of crucible 1: 52.0120 [g] Weight of crucible 2: 57.6055 [g] |
| Method 2 (acid insoluble ash) | Additional for this Hydrogel a concentration step to dryness was done by drying at 105° C. in an normal oven Sample: 25 mL of Hydrogel CVHC Usually 1-2 g Sample weight: usually 1-2 g or sufficient amount to obtain a residue of minimum 1 g. Moisten the sample with a small amount of sulfuric acid R [95-97% m/m] (usuallyl mL) and heat at as low temperature as practicable until the residue is charred. After cooling, moisten the residue with a small amount of sulfuric acid R [95-97% m/m](usuallyl mL) Heat until white fumes are no longer evolved Ignite at 600 +/− 50° C. for 30 min until the residue is completely incinerated. Flames are not allowed to be produced at any time during the procedure allow to cool in a desiccator over silica gel or other suitable desiccant Weigh and calculate the percentage of residue |
| Weighting of total weight | Total Weight of crucible 1: 52.0668 g Total Weight of crucible 2: 57.6612 g |
| Sulphated ash content | Value 1: 0.0548 g Value 2: 0.0557 g Average: 0.05525 g/25 mL |
| Calculation of content of sulphated ash | 0.05525 g/25.05 g = 0.0022055 g/g = 2.2055 mg/g 0.22% |

EXAMPLE 40. LOSS ON DRYING

Based on this Phytochem® established appropriate methods for the determination of loss on drying.

1. Method and Parameter for Test of Chitosan HCl, Chitosan and Chitosan HAc

Sample Preparation

Pretreatment of container: The substance is placed in a suitable weighing bottle, previously dried under the conditions used afterwords Filling: the material is filled not higher than 5 millimeter Transport: The weighing bottle is closed with a suitable cover PC-method: A "under higher vacuum"

modified Pharmacopoeia-method 2.2.32 (EP) "in vacuum in a desiccator"

Apparatus: desiccator

Drying time: to constant weight

Drying temperature: 25° C.±2° C.

Vacuum: permanent 4-8 mbar with specific pumps

Drying reagent: Diphosporuspentoxide (freshly)

2. Estimation of the Loss on Drying of Chitosan in Chitosan-Valeric Acid-Hydro-Colloid (Special Method)

The content of Chitosan in Chitosan-Valeric acid-Hydro-Colloid is estimated with a gravimetric measurement.

Apparatus: Speed circulating vacuum concentrator

Method: Estimation of the loss on drying (special method)

Conditions of Measurement

Pressure: 5 mbar

Temperature: 60° C.

Time: 1 week

End point: Constant mass

Appearance: Glassy mass

Measurement: Test solution 4 ml Chitosan-Valeric acid-Hydro-Colloid

Repetition: 10 times

Result Odor: No typical odor from valeric acid

Weighing

| | |
|---|---|
| 1 | 40.20 mg |
| 2 | 39.80 mg |
| 3 | 40.20 mg |
| 4 | 39.90 mg |
| 5 | 40.10 mg |
| 6 | 40.10 mg |
| 7 | 39.90 mg |
| 8 | 39.60 mg |
| 9 | 40.20 mg |
| 10 | 40.40 mg |

Average 40.04 mg

Standard deviation 0.236643191

Relative standard deviation 0.591016961

Variance 0.056

Results: The weighing of the dried substance shows good similarity. Based on this measurements the content of Chitosan in Chitosan-Valeric acid-Hydro-Colloid is 1%.

3. Comparison of the Results

| | Chitsoan solid | Chitsoan HCl solid | Chitsoan HAc solid | Chitosan-Valeric acid-Hydro-Colloid |
|---|---|---|---|---|
| Loss on drying | 7.2% | 7.9% | 20.3% | . |
| Residue from drying | . | . | . | 1% |
| Target EP | . | <10% | . | . |

The active principle should be a Hydro Colloid gel. The measured data confirm the structure of compound.

EXAMPLE 41. ESTIMATION OF THE OSMOLARITY

The estimation of the Osmolarity can be done was an indirect measurement of the decrease of the melting point of a solution.

Apparatus: Halbmicro Osmometer Knauer

Conditions of measurement: External cooling system

Range: 0-1600 mOsmol

Method: Freezing

Test Procedure

Calibration with Standard solution 400 mOsmol/Kg: 12,687 g NaCl in 1 l Wasser at 20° C.

Repetition: 2 times

Vessel: Specific glass vial

Sample: Chitosan-Valeric acid-Hydro-Colloid

Test solution: 1 without dilution

2 Dilution of 1:5

Quantity 150 µl each

Calibration

| Sample | Spezification | Setpoint | Measured value |
|---|---|---|---|
| Calibration 1 | Bidest. water | 0 mOsmol | 0 mOsmol |
| Calibration 2 | 400 m Osmol/kg | 400 mOsmol | 400 mOsmol |

Measurement

| Number | Sample | Measured value |
|---|---|---|
| 1a | Chitosan-Valeric acid-Hydro-Colloid | 100 mOsmol |
| 1b | Chitosan-Valeric acid-Hydro-Colloid | 110 mOsmol |
| 2a | Chitosan-Valeric acid-Hydro-Colloid | 1:5 20 mOsmol |
| 2b | Chitosan-Valeric acid-Hydro-Colloid | 1:5 20 mOsmol |

Results: The measurement of the Osmorarity of Chitosan-Valeric acid-Hydro-Colloid show a relatively low content. The measured content of osmolar reacting components can only be so low, if there is no solution or suspension of chitosans and valeric acid. The high viscous gelling compound can only be a Hydro-Colloid.

Result: The measured data above confirms the identity of the proposed substance.

The invention claimed is:

1. A method of treating digital dermatitis, interdigital dermatitis or interdigital phlegmon in a cow comprising administering to said cow an effective amount of antigenic material comprising an antigen of a keratinophilic fungus and/or a keratinophilic yeast.

2. The method of claim 1, wherein the antigenic material of said keratinophilic fungus and/or yeast comprises homogenised inactivated dermatophyte microconidia and/or homogenised inactivated yeast blastospores and/or antigenic material of dermatophyte microconidia and/or antigenic material of yeast blastospores.

3. The method of claim 2, wherein the antigenic material of dermatophyte microconidia and/or antigenic material of yeast blastospores comprise antigenic material, not soluble in aqueous solutions, comprising polysaccharide and/or glycopeptide (ANMP), antigenic material, soluble in aqueous solutions, comprising polysaccharide and/or glycopeptide (ASMP) or antigenic exogenous material comprising polysaccharide and/or glycopeptide (AEMP).

4. The method of claim 1, wherein the antigenic material of keratinophilic fungi and/or keratinophilic yeasts are derived from *Trichophyton, Microsporum*, and/or *Candida*.

5. The method of claim 1, wherein the antigenic material of keratinophilic fungi is derived from the strains *Trichophyton mentagrophytes* DSM-7279, *Trichophyton verrucosum* DSM-28406, *Trichophyton rubrum* DSM-9469, *Trichophyton rubrum* DSM-9470, *Trichophyton rubrum* DSM-9471, or *Trichophyton rubrum* DSM-9472 and/or the antigenic material of keratinophilic yeasts is derived from the strains *Candida albicans* DSM-9456, *Candida albicans* DSM-9457, *Candida albicans* DSM-9458, or *Candida albicans* DSM-9459.

6. The method of claim 2, wherein the microconidia are in a swollen condition and/or have germ tubes.

7. The method of claim 2, wherein the blastospores and/or microconidia have been inactivated with thiomersal, formaldehyde and/or 2-propionlactone.

8. The method of claim 1, wherein the composition additionally comprises one or more immunomodulatory substances.

9. The method of claim 1, wherein the composition comprises additionally chitosan modified by valeric acid, lactic acid, para-aminobenzoic acid, glucuronic acid or chloride of valeric acid or a hydro colloid comprising:
   (i) 0.1% to 5% (w/v) chitosan and 0.001 to 5% (w/v) valeric acid, or a salt thereof, or
   (ii) 0.1% to 5% (w/w) chitosan and 0.001 to 5% (w/w) glucuronic acid or p-aminobenzoic acid or a salt thereof.

10. The method of claim 1, wherein the composition is a pharmaceutical composition.

11. A composition comprising *Trichophyton verrucosum* strain DSM-28406, homogenised inactivated dermatophyte microconidia of *Trichophyton verrucosum* DSM-28406 or antigenic material comprising antigens of *Trichophyton verrucosum* strain DSM-28406 including ANMP, AEMP and ASMP of dermatophyte microconidia of *Trichophyton verrucosum* DSM-28406.

12. A vaccine formulation comprising *Trichophyton verrucosum* strain DSM-28406, homogenised inactivated dermatophyte microconidia of *Trichophyton verrucosum* DSM-28406 or antigenic material comprising antigens of *Trichophyton verrucosum* strain DSM-28406 including ANMP, AEMP and ASMP of dermatophyte microconidia of *Trichophyton verrucosum* DSM-28406.

13. A method of treating digital dermatitis, interdigital dermatitis, or interdigital phlegmon in a cow comprising administering to said cow an effective amount of *Trichophyton verrucosum* DSM-28406, homogenised inactivated dermatophyte microconidia of *Trichophyton verrucosum* DSM-28406 or antigenic material comprising antigens of *Trichophyton verrucosum* strain DSM-28406 including ANMP, AEMP and ASMP of dermatophyte microconidia of *Trichophyton verrucosum* DSM-28406.

14. The method of claim 4, wherein the antigenic material of keratinophilic fungi and/or keratinophilic yeasts are derived from *Trichophyton verrucosum, Trichophyton mentagrophytes, Trichophyton equinum, Trichophyton sarkisovii, Trichophyton rubrum Trichophyton mentagrophytes, Microsporum gypseum, Microsporum canis*, and/or *Candida albicans*.

15. The method of claim 14, wherein the antigenic material of keratinophilic fungi and/or keratinophilic yeasts are derived from *Microsporum canis* var. *obesum* or *Microsporum canis* var. *distortum*.

16. The method of claim 11, wherein the valeric acid, is chloride of valeric acid.

* * * * *